United States Patent
Sato et al.

(10) Patent No.: US 10,980,498 B2
(45) Date of Patent: Apr. 20, 2021

(54) RADIOGRAPHY APPARATUS

(71) Applicant: SHIMADZU CORPORATION, Kyoto (JP)

(72) Inventors: Shota Sato, Kyoto (JP); Wataru Takahashi, Kyoto (JP); Michel Dargis, Kyoto (JP); Takihito Sakai, Kyoto (JP); Keiichi Goto, Kyoto (JP); Sebastien Matte, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/066,568

(22) PCT Filed: Dec. 28, 2015

(86) PCT No.: PCT/JP2015/086553
§ 371 (c)(1),
(2) Date: Aug. 1, 2018

(87) PCT Pub. No.: WO2017/115432
PCT Pub. Date: Jul. 6, 2017

(65) Prior Publication Data
US 2019/0015056 A1 Jan. 17, 2019

(51) Int. Cl.
*A61B 6/00* (2006.01)
*A61B 6/12* (2006.01)
*G06K 9/46* (2006.01)

(52) U.S. Cl.
CPC ............. *A61B 6/12* (2013.01); *A61B 6/485* (2013.01); *A61B 6/487* (2013.01); *A61B 6/504* (2013.01);
(Continued)

(58) Field of Classification Search
CPC .................................. A61B 6/12; A61B 6/485
See application file for complete search history.

(56) References Cited

U.S. PATENT DOCUMENTS

| | | | |
|---|---|---|---|
| 9,613,289 B2 * | 4/2017 | Sakaguchi | A61B 6/504 |
| 2013/0129144 A1 * | 5/2013 | Chang | G06K 9/62 382/103 |
| 2013/0156267 A1 * | 6/2013 | Muraoka | G06T 7/0016 382/103 |

FOREIGN PATENT DOCUMENTS

| | | |
|---|---|---|
| JP | 2015-128578 | 7/1916 |
| JP | 2005-510288 | 4/2005 |

(Continued)

OTHER PUBLICATIONS

PCT/JP2015/086553, International Search Report and Written Opinion dated Apr. 5, 2016, 5 pages—English, 5 pages—Japanese.

*Primary Examiner* — Tuan H Nguyen
(74) *Attorney, Agent, or Firm* — Andrew F. Young, Esq.; Nolte Lackenbach Siegel

(57) ABSTRACT

A radiography apparatus sequentially determines, on the basis of the positions of markers as time-sequential feature points (of a plurality of frames), positions at which the markers in the frames are displayed. This makes it possible to display a moving object while the position, direction and size thereof are properly set. Another advantage is that when a plurality of markers are extracted, information relating to the direction and size of the object is retained and the proximal and distal directions of the object and the length of a device (e.g., stent) can be intuitively determined from an image. Since positioning is performed using the plurality of positions of markers and the plurality of display positions, the position and direction of a corrected image to be finally displayed can also be set properly.

11 Claims, 15 Drawing Sheets

(52) U.S. Cl.
CPC .............. *A61B 6/52* (2013.01); *A61B 6/5264* (2013.01); *G06K 9/4604* (2013.01); *A61B 6/4441* (2013.01); *G06T 2207/10116* (2013.01); *G06T 2207/30204* (2013.01)

(56) References Cited

FOREIGN PATENT DOCUMENTS

| | | |
|---|---|---|
| JP | 2008-520320 | 6/2008 |
| JP | 2010-131371 | 6/2010 |
| JP | 2013-46750 | 3/2013 |
| JP | 2013-521969 | 6/2013 |
| JP | 2014-50747 | 3/2014 |

* cited by examiner

P$_{20}$

P_{20}

RADIOGRAPHY APPARATUS

CROSS REFERENCE TO RELATED APPLICATION

This application relates to, and claims priority from, Ser. No.:PCT/JP2015/086553, filed Dec. 28, 2015, the entire contents of which are incorporated herein by reference.

FIGURE FOR PUBLICATION

FIGS. 5A, 5B

BACKGROUND OF THE INVENTION

Field of the Invention

The present invention relates to a radiography apparatus that acquires a plurality of radiographs based on detected radiations and particularly, relates to a technology for extraction of a plurality of feature points that a predetermined target object has based on the radiograph.

Description of the Related Art

With regard to the technology for extraction of a plurality of feature points that the predetermined target object has based on the radiograph, such a predetermined target object is a blood vessel of a subject and a device being inserted into the inside of the body of the subject. Hereinafter, the inventor sets forth e.g., an X-ray as such a radiation. The device being inserted into the inside of the body of the subject is e.g., a stent that is applied to the intervention therapy, a marker attached to the stent, a probe applied to an intravascular ultrasound (IVUS), a catheter that is applied to a cardiovascular ultrasound and so forth.

When the device is inserted into the inside of the body of the subject, the feature point is extracted, and the aligning is carried out based on such a feature point, so that the device is highlighted and displayed by carrying out a time integration in which X-ray images having a plurality of frames are superimposed (e.g., Patent Documents 1-4).

More specifically, according to Patent Document 1, JP2005-510288, the feature point of the target object is extracted, the reference (marker) of the target object is aligned, the time integration of the aligned target object is carried out together with the background thereof and the integrated image is highlighted and displayed on the faded (i.e., dim) background.

In addition, according to Patent Document 2: JP 2008-520320, at least two feature points are extracted from the region of interest (ROI), each feature point is aligned individually and the individually aligned image is generated, and each aligned image is weighted and added to generate the superimposed image of the target object (object of interest).

In addition, according to Patent Document 3: JP2010-131371, the position of the target object is extracted, each image is aligned to the feature point relative to the reference image of the past-frame, and the aligned image is displayed in real-time.

In addition, according to Patent Document 3: JP2010-131371, the correction image is generated by aligning based on the periodic trajectory of the reference point (marker) of the target object.

RELATED PRIOR ART DOCUMENTS

Patent Document

Patent Document 1—JP 2005-510288
Patent Document 2—JP 2008-520320
Patent Document 3—JP 2010-131371
Patent Document 4—JP 2013-521969

ASPECTS AND SUMMARY OF THE INVENTION

Objects to be Solved

However, despite such an alignment set forth above, it is problematic that the moving target object is not always provided with an adequate position, direction and size to be displayed.

With regard to a percutaneous transluminal coronary angioplasty (PTCA), the guide-wire (catheter) with a stent is inserted into the stenosed (narrowed) affected area of the subject (patient) and the stent must be indwelt in the accurate location while watching the X-ray fluoroscopic image under the condition in which the heart of the patient is beating. In addition, with regard to transcatheter aortic valve replacement (TAVR), the prosthetic valve must be indwelt in the accurate location as well as PTCA. Particularly, in the case of TAVR, given the indwelt location or angle of the prosthetic valve is erroneous and the (indwelt) prosthetic valve is fallen, such an incident may provide the patient with a fatal impact, so that the surgeon (operator) is required to make an extremely cautious positioning.

Therefore, according to the methods disclosed in the above Patent Document 1: JP 2005-510288, Patent Document 2: JP 2008-520320, and Patent Document 3: JP 2010-131371, as the feature point of the moving target object is fixed and then displayed, a likelihood of an accurate positioning of the target object such as a stent is being pursued. The location fixing the feature point of the target object is proposed to be a location of the target object of the first frame or a predetermined location on the screen in advance.

Whereas the location of the target object of the first frame is the fixed location, direction and size of the target object, such a location is not always adequate for the surgeon (operator). In addition, given the feature point is fixed to the predetermined location, the information (data) relative to the inherent direction and size of the target object is completely lost, so that it is hard for the operator to intuitively distinguish between a proximal blood vessel and a distant blood vessel and understand the length of the stent referring to the image. In addition, the information are displayed in real-time, so that the operator is hard to manually select the frame of the adequate fixed location.

Therefore, it is considerable that the correction image is generated by aligning based on the periodical trajectory of the marker of the device according to Patent Document 4, JP2013-521969, as listed above, but the target object of such a marker located on the periodical trajectory is as-is and is not always located in the accurate location.

Considering such circumstances, the object of the present invention is to provide a radiography apparatus that sets up the moving (dynamic) target object to be in an adequate location, direction and size.

Means for Solving the Problem

The present invention comprises the following structure to achieve such objects.

Specifically, a radiography apparatus of the first present invention, which is the radiography apparatus that acquires a plurality of radiographs based on detected radiations, comprises a radiograph generation circuit that sequentially generates time-series the radiographs based on a radiography in which a radiation is irradiated to a subject and the radiation transmitting through the subject is detected, a feature point location acquisition circuit that extracts locations of a plurality of feature points that a predetermined target object possesses based on the radiographs generated in series and acquires time-series locations of the plurality of feature points, a feature point display-location determination circuit that determines in series the respective locations of the plurality of feature points to be displayed as respective display-locations of the target object based on the location of time-series the target object acquired in series, a correction image generation circuit that sequentially generates time-series correction images as a correction image that is radiograph acquired by aligning the radiographs following aligning the locations, so that the location of each feature point coincides with the display-location, and a display control circuit that controls the correction images to be displayed in series The radiography apparatus according to the first invention determines the display-location of respective feature points of such frames in-series based on the locations of the feature points (of a plurality of frames) time-series, so that such a radiography apparatus can display the moving target object that is set up so as to have an adequate location, direction and size thereof. In addition, a plurality of feature points is extracted, so that the information of the direction and size of the target object is maintained, and it is effectively distinguishable whether the target object (e.g., blood vessel) is proximal or distant and the length of the device (e.g., stent) can be understood intuitively from the image. In addition, the alignment is executed using both the locations of a plurality of feature points and a plurality of display-locations, so that the correction image per se that are displayed at the end can be set up so as to have the accurate location and direction.

In addition, according to the first invention, the feature points can be extracted a plurality of times relative to respective radiographs that are generated in series. Needless to say, the feature point can be extracted just once also.

In addition, according to the first invention, it is preferable that a predetermined location is calculated based on the location of time-series and the calculated predetermined locations are determined as respective locations of a plurality of feature points to be displayed in series. The display-location of the feature point can be determined adequately and automatically based on such a calculation. Particularly, when the locations of respective time-series feature points are averaged, the movement of the display-location becomes gradually slow and converges to the average location of respective feature points due to the movement (e.g., beat) at the end. Therefore, the moving target object can be fixed to have the average location, the average direction and the average size and then displayed at the end. In addition, the process to reach the end is gradually, slowly and naturally proceeds without an unnatural sensation. In addition, given the median value of the locations of the respective time-series feature points is used, the location of the feature point is further strong despite missing a frame due to a mistake relative to the extraction of the feature point.

In addition, when the locations of respective time-series feature points are averaged, the feature point is fixed to the predetermined location from the initial frame, the change of rotation and size of such a feature point as the center thereof becomes gradually slow, and then as set forth above, the target object can be displayed while fixing the target object to the average direction and size at the end. Regardless the location of the target object on the screen, the display can display the feature point in an adequate location. In addition, when average the locations of the respective time-series feature points or use the median value of the respective time-series feature points, the respective display-locations of the feature points is specified as the average of locations of the plurality of feature points or the median value thereof, so that the adequate location of the target object can be displayed in the center of the display (screen) at the end.

In addition, according to the first invention, the feature point display-location determination circuit comprises a target object location acquisition circuit that determines a location of the target object based on the locations of a plurality of feature point locations in series and acquires such a determined location of the target object in series, wherein, alternatively, the feature point display-location determination circuit determines in series respective locations of the plurality of feature points that should be displayed as the respective display-locations of the plurality of feature points so that the location of the target object is a predetermined location while keeping the locations of the plurality of feature points relative to the location of the target object. In such a case, the moving target object is set up in the adequate location and direction while keeping the length and size of the target object.

Even in such a case, it is preferable that a predetermined location is calculated based on the locations of a plurality of feature points and the calculated predetermined locations are acquired as the location of the feature point. The display-location of the feature point of the target object can be determined adequately and automatically based on such a calculation.

In addition, a radiography apparatus, according to an alternative invention to the first invention, that acquires a plurality of radiographs based on detected radiations comprises a radiograph generation circuit that sequentially generates time-series said radiographs based on a radiography in which a radiation is irradiated to a subject and said radiation transmitting through said subject is detected, a feature point location acquisition circuit that extracts locations of a plurality of feature points that a predetermined target object possesses based on the radiographs generated in series and acquires time-series locations of the plurality of feature points, a target object location acquisition circuit that determines a location of the target object based on the locations of the plurality of feature points every same frame extracted in series and acquires time-series locations of said target object in series, a target object direction acquisition circuit that determines a direction of the target object based on locations of said plurality of feature points every same frame extracted in series and acquires time-series directions of the target object in series, a target object display-location determination circuit that determines in series a display-location of the target object to be displayed based on locations of the time-series target object acquired in series, a target object display-direction determination circuit that determines in series a display-direction of the target object to be displayed based on a direction of the time-series target object acquired in series, a correction image generation circuit that sequentially generates time-series correction images as a correction image that is a radiograph following aligning the locations acquired by aligning the locations of the radiographs so that the location of the target object coincides with the display-location and also, the direction of the target object coincides with the display-direction of the target object, and a display control circuit that controls the correction images to be displayed in series.

The radiography apparatus according to the second invention determines the display-location and display-direction of respective feature points of such frames in-series based on the locations and directions of the time-series feature points (of a plurality of frames), so that such a radiography apparatus can display the moving target object that is set up so as to have an adequate location and direction thereof. In addition, the direction of the target object is displayed under consideration of the direction of the target object based on a plurality of feature points, so that even when the direction changes, the target object per se is not deformed and as a result, the form of the target object is never unnatural. In addition, a plurality of feature points is extracted, so that the information of the direction and size of the target object is maintained, and it is effectively distinguishable whether the target object (e.g., blood vessel) is proximal or distant and the length of the device (e.g., stent) is understandable intuitively from the image. In addition, the alignment is executed using both the location and direction of the target object, so that the correction image per se that are displayed at the end can be set up so as to have the accurate location and direction.

In summary, the first invention and the second invention are different in the following aspects. According to the first invention, movement, rotation (isotropic or anisotropic) expanding, shrinking or deformation takes place. The device (e.g., stent) converges to an average location, an average angle and an average size (form). The size is also averageable, but negatively, anisotropic magnifying, shrinking and deformation likely result in proving an unnatural image. In addition, the calculation cost therefor is larger. According to the second invention, movement and rotation take place. The device (e.g., stent) converges to an average location and an average angle. Even though the size is not averageable, no deformation takes place, so that the image is never unnatural. In addition, the actual change of the size is so small that it is not concerned at all. In addition, the calculation cost therefor is smaller.

In the pre-step for determining the display-location of the target object and the display-direction thereof, the location and direction of the target object that are the bases of the display-location and display-direction of the target object can be determined based on the following calculation. Specifically, a predetermined location is calculated based on locations of a plurality of feature points, acquires such a calculated location as a location of the target object in series, calculates the predetermined direction based on the direction of the regression line relative to the plurality of feature points and acquires such a calculated predetermined direction as a direction of said target object in series. Accordingly, the location and direction of the feature point of the target object can be determined adequately and automatically based on such calculations.

In addition, it is preferable that the predetermined location and direction of the target object are calculated based on the time-series locations and directions acquired in series, and the calculated predetermined locations and directions determined as the display-location and display-direction of the target object in series. According to such calculations, the display-location of the target object and the display-direction thereof can be determined adequately and automatically. Particularly, when average the locations and directions of the target object, the movement of the display-location and the display-direction become gradually slow and converges to the average of movements of the location and direction of the target object due to such movements (e.g., beat) at the end. Therefore, the moving target object can be fixed to have the average location, the average direction and then, displayed at the end. In addition, the process to reach the end is gradually, slowly and naturally proceeds without an unnatural sensation. In addition, given the median value of the locations of the respective time-series feature points is used, the location of the feature point is further strong despite missing the frame due to the mistake relative to the extraction of the feature point.

In addition, when average the locations and directions of the time-series target object or use the median value of the location and directions time-series target object, the display-location and display-direction of the target object is specified as the average of locations of the time-series target objects or the median value thereof, so that the adequate location of the target object can be displayed in the center of the display (screen) and the target object can be set up in the adequate direction.

According to the first invention and the second invention, the predetermined area of the correction image is magnified and then, displayed in series, so that the target object can be observed in more detail. When the feature point and the target object are unified, the location of the target object is known, so that a proximity of the target object can be magnified and displayed. When the feature point and the target object are distant, the location where the target object is present is predicted from the relative location of the target object to the feature point is known, so that such a predicted location can be magnified and displayed. On the other hand, the user such as a surgeon designates the display area and magnifies the desired area and displays such an area.

According to the first invention and the second invention, the correction image generation circuit further comprises a background difference image generation circuit that executes a time subtraction on the time-series radiographs and generates background difference images in series by such a time subtraction, wherein the correction image generation circuit that sequentially generates such time-series correction images as the correction image that is a location aligned background difference image obtained by aligning locations of the background different images. Specifically, the background subtraction by the time subtraction is executed prior to the alignment of the target objects, so that the background subtraction image from which the background having less movement is erased instead of the original image (radiograph) can be displayed. The background difference image in which the background is disappeared in advance is displayed, so that worsening of the visibility of the target region and discomforting due to movement of the background not subjected to the alignment do not take place.

According to the first invention and the second invention, it is preferable that the correction image generation circuit further comprises a time integration correction image circuit that executes a time integration on the time-series correction image and generates a time integration correction image in series by such a time integration, and that the display control circuit controls displaying such a time integration correction image in series. Specifically, the time integration is executed following aligning the locations of the target object, so that noise is cut and the visibility of the fine target object can be improved with low-contrast. The time integration of the background without aligning is executed, so that worsening of the visibility of the target region and discomforting due to movement of the background without aligning can be alleviated.

Effect of the Invention

The radiography apparatus according to the first invention determines the display-location of respective feature points of such frames in-series based on the locations of the feature points (of a plurality of frames) time-series, so that such a radiography apparatus can display the moving target object that is set up so as to have an adequate location, direction and size thereof.

The radiography apparatus according to the alternate invention (second invention) determines the respective display-location and display-direction of feature points of such frames in-series based on the locations and directions of the time-series feature points (of a plurality of frames), so that such a radiography apparatus can display the moving target object that is set up so as to have an adequate location and direction thereof.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
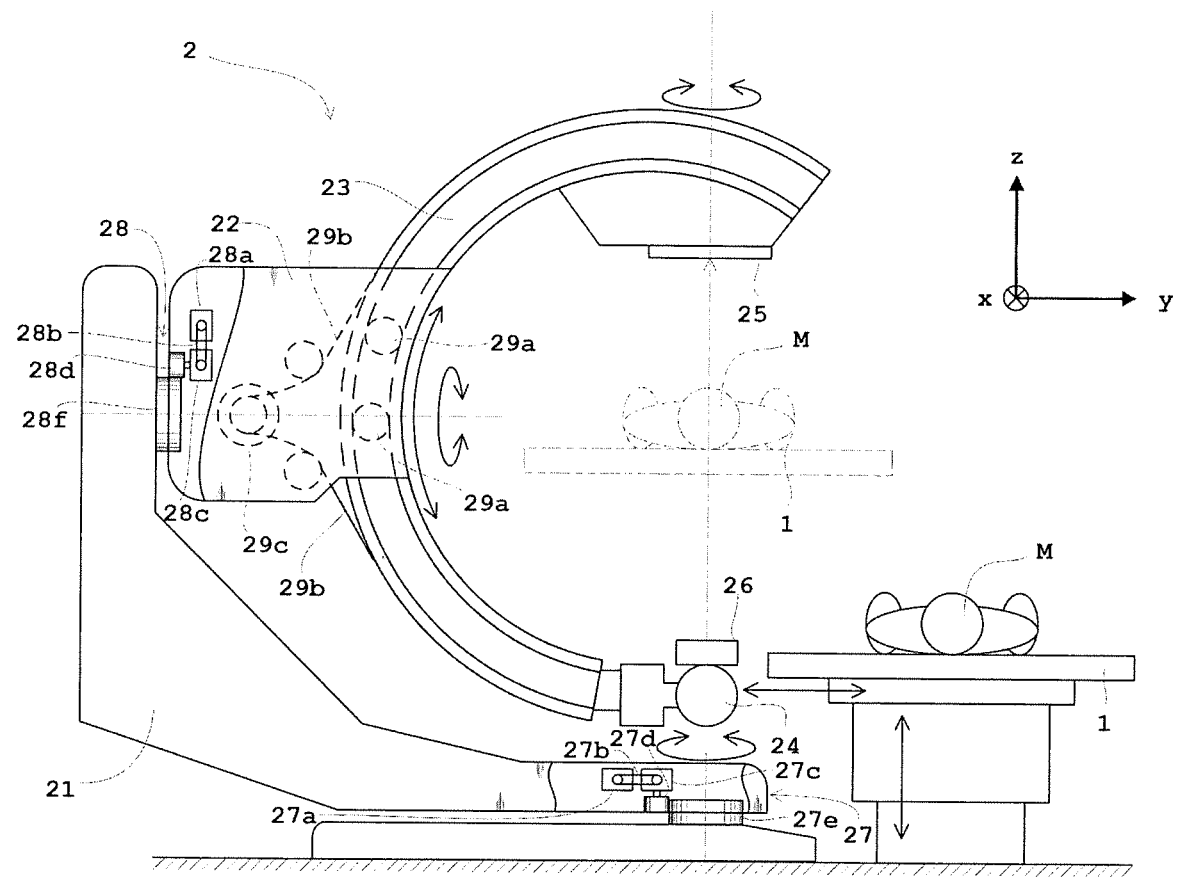
FIG. 1 is a front view of an X-ray apparatus having a C-arm relative to each Embodiment.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 2:
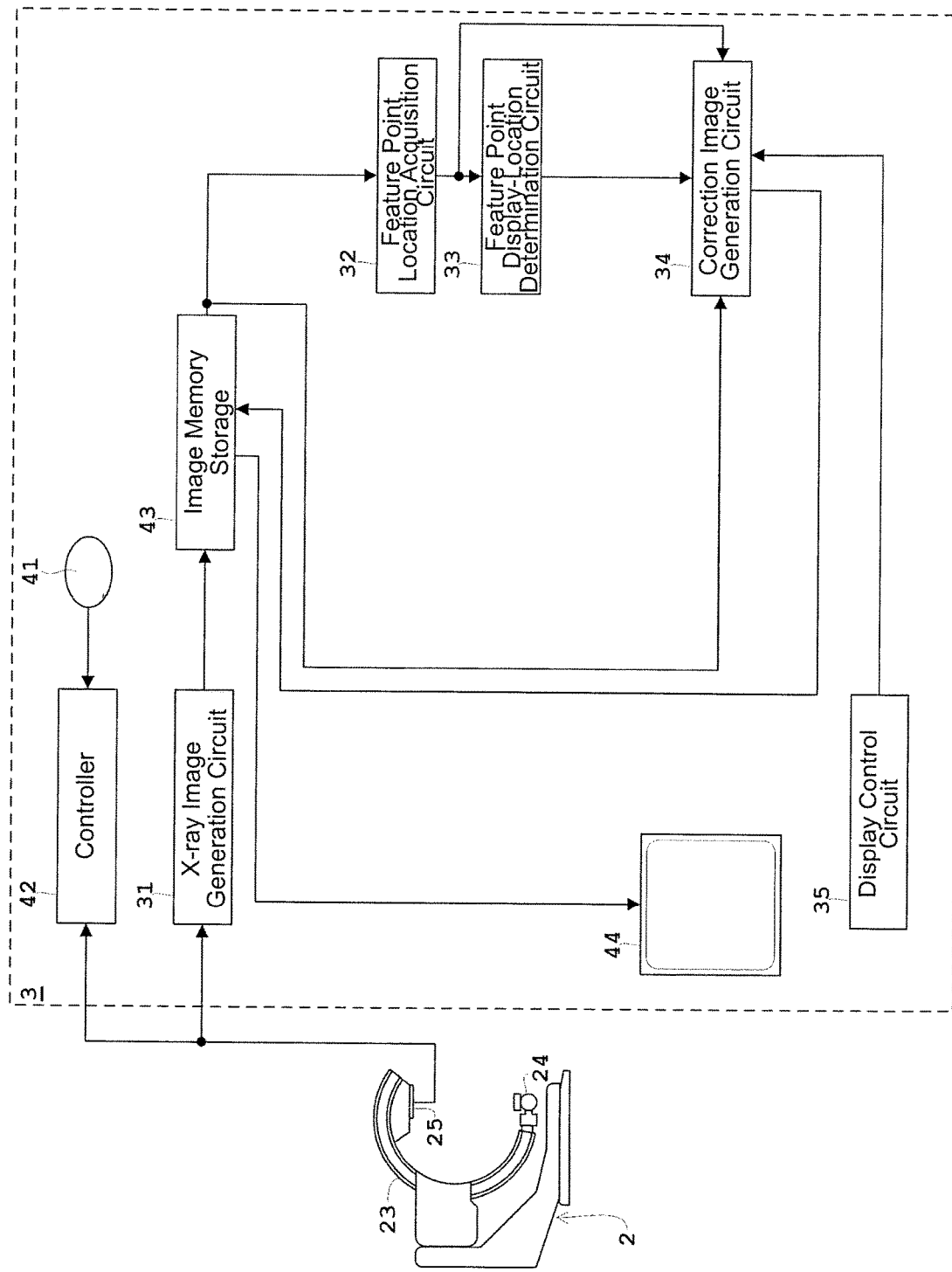
FIG. 2 is a block diagram illustrating the image processing system of the X-ray apparatus according to the aspect of the Embodiment 1.

Referring to FIGs., the inventor sets forth the Embodiment 1 of the present invention. FIG. 1 is a front view of an X-ray apparatus having a C-arm relative to each Embodiment and FIG. 2 is a block diagram illustrating the image processing system of the X-ray apparatus according to the aspect of the Embodiment 1. The inventors set forth X-ray as a radiation in the aspects of the Embodiment 1 and the Embodiment 2 as well as set forth later and the PTCA (percutaneous transluminal coronary angioplasty) as an example of the intervention radiology (IVR) such as an intervention therapy. In addition, referring to FIG. 1, the X-ray apparatus having the C-arm 23 is applied to the CVS (cardiovascular system) apparatus that is used for the cardiovascular diagnosis.

the X-ray apparatus according to the aspects of the Embodiment 1 and the Embodiment 2 as well as set forth later comprises the table 1 on which the subject M is loaded, the imaging system 2 that carries out an imaging for fluoroscopy or video-replay of the subject M referring to FIG. 1 and the image processing system 3 referring to FIG. 2. Referring to FIG. 1, the table 1 is movable vertically and horizontally. Here, the video replay denotes that respective time-series images taken in the past are displayed one by one to play a video and is different from a real-time display such as fluoroscopy.

First, referring to FIG. 1, the inventors set forth the imaging system 2. The imaging system 2 comprises a pedestal 21 installed on the floor (xy-plane in FIG. 1), a C-arm support element 22 that the pedestal 21 supports, a C-arm 23 that the C-arm support element 22 supports, an X-ray tube 24 supported at the one end of the C-arm 23 and the flat panel type X-ray detector (FPD) 25 supported at the other end thereof. A collimator 26 that controls the bright visual field 23 is installed in the irradiation side of the X-ray tube 24 that the C-arm 23 supports at the one end thereof.

In addition, the first imaging system movement element 27 that rotates and moves the pedestal 21 around the vertical axis (z-axis in FIG. 1). The first imaging system movement element 27 comprises a motor 27a, a belt 27b that transmits rotation of the motor 27a, a gear box 27c that changes the rotation transmitted to the belt 27b to the rotation around the vertical axis, a gear 27d that transmits the rotation around the vertical axis from the gear box 27c, and a gear 27e that gears the gear 27d. The gear 27e is fixed on the floor surface with a bearing, not shown in FIG., in-between. When the motor 27a is driven and rotates, the gear 27e rotates around the vertical axis via the belt 27a and the gear 27d, so that the pedestal 21 rotates and moves around the vertical axis relative to the floor surface in accordance with rotation of the gear 27e. In addition, the pedestal 21 rotates and moves around the vertical axis according to the first imaging system movement element 27, so that the C-arm support element 22 that the pedestal 21 supports also rotates and moves around vertical axis, the C-arm 23 that the C-arm support element 22 supports rotates and moves around the vertical axis, the X-ray tube 24 and the flat panel type X-ray detector (FPD) 25 that the C-arm 23 supports also rotate and move around the vertical axis. As set forth above, the first imaging system movement element 27 rotates and moves the imaging system 2 around the vertical axis.

In addition, the imaging system 2 further comprises the second imaging system movement element 28 that rotates and moves the C-arm support element 22 relative to the pedestal 21 around the orthogonal axis (y-axis in FIG.) to the body axis (x-axis in FIG.) of the subject M in the horizontal plane. The second imaging system movement element 28 comprises a motor 28a, a belt 28b that transmits rotation of the motor 28a, a gear box 28c that changes the rotation transmitted to the belt 28b to the rotation around the orthogonal axis to the body axis in the horizontal plane, a gear 28d that transmits the rotation around the orthogonal axis to the body axis in the horizontal plane from the gear box 28c, and a gear 28e that gears the gear 28d. The gear 28e is fixed to the pedestal 21 with a bearing, not shown in FIG., in-between. When the motor 28a is driven and rotates, the gear 28e rotates around the orthogonal axis to the body axis in the horizontal plane via the belt 28b, the gear box 28c and the gear 28d, so that the C-arm 22 relative to the pedestal 21 rotates and moves around the orthogonal axis to the body axis in the horizontal plane in accordance with rotation of the gear 28e. In addition, the C-arm 23 that the C-arm support element 22 supports also rotates and moves around the orthogonal axis to the body axis in the horizontal plane, both the X-ray tube 24 and the FPD 25 that the C-arm 23 supports rotate and move around the orthogonal axis to the body axis in the horizontal plane. As set forth above, the second imaging system movement element 28 rotates and moves the imaging system 2 around the orthogonal axis to the body axis in the horizontal plane.

In addition, the imaging system 2 further comprises the third imaging system movement element 29 that rotates and moves the C-arm around body axis (x-axis in FIG.) of the subject M. The C-arm is formed as a kind of rail, and the third imaging movement element 29 comprises two bearings 29a connecting with the groove of the C-arm 23, a belt 29b that is attached along the circumference surface of the C-arm 23, and a motor 29c that winds a part of the belt 29b. When the motor 29c is driven and rotates, the belt 29b goes around and the C-arm 23 slides relative to the bearing 29a along with rounding. The C-arm 23 rotates and moves around the body axis along with such sliding. In addition, both the X-ray tube 24 and the FPD 25 that the C-arm 23 supports also rotates and moves around the body axis. As set forth above, the third imaging system movement element 29 rotates and moves the imaging system 2 around the body axis.

As set forth above, the C-arm 23 that supports the X-ray tube 24 and the FPD 25 is bended and formed as letter C along the rotation and movement direction around the body axis by the third imaging system movement element 29 and in other words, the X-ray tube 24 and the FPD 25 rotate and move around the body axis along the bending direction of the C-arm 23. In addition, the second imaging system movement element 28 rotates and moves the C-arm in the direction around the orthogonal axis to the body axis in the horizontal plane, which is different from the direction of the rotation and movement of the C-arm around the body axis, and in other words, the imaging system 2 rotates and moves the C-arm around the orthogonal axis to the body axis in the horizontal plane.

Other than the above components, the imaging system 2 further comprises an imaging system moving element (not shown in FIG.) that translates the imaging system 2 in the horizontal direction by translating the pedestal 21, and the C-arm support element 22 or the C-arm 23 in the horizontal direction (e.g., x-direction or y-direction in FIG.), and the C-arm comprises an FPD moving element (not show in FIG.) that rotates and moves the FPD 25 around the support axis supporting the FPD 25. In addition, the imaging system 2 may comprise an imaging system adjustment element (not show in FIG.) that rotates and moves the C-arm to adjust the flexure (locational shift) due to the weight of the C-arm per se or the weight of the X-ray tube 24 and the FPD 25 per se. In addition, the imaging system 2 may comprise an imaging system lifting element (not show in FIG.) that translates the imaging system 2 along the vertical axis by moving up-and-down the C-arm supporting element 22 or the C-arm 23 along the vertical axis.

In addition, the C-arm may comprise an FPD moving element (not show in FIG.) that translates the FPD 25 along the support axis supporting the FPD 25. In such a case, the supporting axis supporting the FPD 25 is parallel to the vertical line direction (i.e., irradiation center axis) from the X-ray tube 24 to the FPD 25, so that the C-arm 23 translates the FPD 25 in the vertical direction by that the FPD moving element translates the FPD 25 along the supporting axis. Specifically, the FPD moving element varies the distance between the X-ray tube 24 and the FPD 25 along the vertical line (i.e., SID (Source-to-Image-Receptor Distance) and translates the imaging system 2 along the vertical line.

The image processing system 3, set forth later, processes the X-ray detection signal obtained by the FPD 25 and detects the X-ray irradiated from the X-ray tube 24 by moving the table 1 and the imaging system 2 as set forth above to provide the X-ray image of the subject M. Particularly, with regard to the fluoroscopy or imaging for a video-replay, the X-ray tube and the FPD are set up at the desired location, the subject M is loaded on the table 2 prior to an administration of a contrast agent and the X-ray image (original image) of the subject M is obtained while leaving the subject M subject to the desired posture. The inventors set forth later respective images and an image processing on such images.

Next, referring to FIG. 2, the inventors set forth the image processing system 3. With regard to a fluoroscopy and an imaging for video-replay, an image processing system 3 comprises the X-ray image generation circuit 31 that sequentially generates time-series X-ray images (original images) $P_{10}$ (referring to FIG. 3) that are projected on the detection surface of the FPD 25 based on the X-ray detection signal, the feature point location acquisition circuit 32 that extracts locations of a plurality of feature points that a predetermined target object possesses based on such X-ray images (original images) $P_{10}$ generated in series and acquires time-series locations of the plurality of feature points in series, the feature point display-location determination circuit 33 that determines in series the respective locations of the plurality of feature points to be displayed as respective display-locations of the feature points based on the location of the time-series feature points acquired in series, the correction image generation circuit 34 that sequentially generates time-series correction images $P_{20}$ as the correction image $P_{20}$ (referring to FIG. 6) that is the X-ray image following aligning the locations acquired by aligning the X-ray images (original images) $P_{10}$ so that each feature point coincides with each display-location, and a display control circuit 35 that controls the correction images $P_{20}$ to be displayed in series.

The X-ray image generation circuit 31 corresponds to the radiography generation means of the present invention, the feature point acquisition circuit 32 and the input element 41, set forth later, correspond to the feature point acquisition means of the present invention, the feature point display-location determination circuit 33 corresponds to the feature point display-location determination means of the present invention, the correction image generation circuit 34 corresponds to the correction image generation means of the present invention, and the display control circuit 35 corresponds to the display control means of the present invention.

Other than the above, the image processing system 3 comprises: an input element 41 that designates manually the location of the feature point by inputting the feature point represented by such as a marker and so forth, a controller 42 that controls each component of the image processing system 3, a memory storage element 43 that stores once the respective images such as X-ray images (original images) $P_{10}$ and the correction image $P_{20}$ and so forth that are obtained while imaging particularly for the video-replay, and a monitor 44 that displays the location and direction of the feature point (particularly, the correction image $P_{20}$ obtained at the end).

In addition, the input circuit 12 that is for inputting the data and directive, which the user inputs, comprises a pointing device represented by a mouse, a keyboard, a joy stick, a trackball and a touch panel and so forth. The controller 42 comprises such as a central processing unit (CPU) and so forth. The memory element 43 comprises a memory media represented by a RAM (random-access memory) and so forth. In addition, referring to FIG. 2, for the convenient drawing FIG., a connection line between the controller 42 and the components, which the controller 42 controls, is not shown for the convenient drawing FIG.

The X-ray image generation circuit 31 sequentially generates time-series X-ray images (original images) $P_{10}$ based on X-ray imaging in which X-rays are irradiated toward the subject M and the X-rays transmitting through the subject M is detected (by FPD 25). The X-ray images (original images) $P_{10}$ generated in series are sent to the image memory storage 43. In addition, in the case of fluoroscopy, the X-ray images (original images) $P_{10}$ without being sent to be stored in the image memory storage 43 are sent to the feature point location acquisition circuit 32 to display the images in real time. Needless to say, given it is not problematic even when the time-lag takes place somewhat, the X-ray images (original images) $P_{10}$ can be sent to the image memory storage 43 upon fluoroscopy.

The X-ray images (original images) $P_{10}$ generated in series are written and stored in the memory storage 43. The X-ray images (original images) $P_{10}$ stored in the image memory storage 43 are read out and sent to the feature point location acquisition circuit 32 and the correction image generation circuit 34 to extract the location of the feature point and acquire or align therefor.

The feature point location acquisition circuit 32 extracts locations of a plurality of feature points that a predetermined target object possesses based on such X-ray images (original images) $P_{10}$ generated in series and acquires time-series locations of the plurality of feature points in series. The time-series locations of the plurality of feature points that are acquired in series are sent to the feature point display-location determination circuit 33 and the correction image generation circuit 34. In addition, arbitrarily and according to necessity, the time-series locations of the plurality of feature points that are acquired in series are written and stored in a memory medium such as a RAM and so forth.

The feature point display-location determination circuit 33 determines in series that the respective locations of the plurality of feature points subject to display are respective display-locations of the feature points based on the location of the time-series feature points acquired in series. According to the aspect of the Embodiment 1, the feature point display-location determination circuit 33 calculates a predetermined location based on the location of each time-series feature point and determines that such calculated predetermined locations subject to display are the respective locations of plurality of feature points to be displayed in series. The specific calculation is not particularly limited, but the average value of the respective time-series feature points or the median value thereof is determined in series as the respective display-locations of the target object. Other than the above, for example, the mode value may be determined as the respective display-locations of the target object in series. The inventors set forth the specific movements of the feature point (marker) and the above calculated display-location later referring to FIGS. 5A, 5B. Each display-location is sent to the correction image generation circuit 34.

The correction image generation circuit 34 that sequentially generates time-series correction images $P_{20}$ as the correction image $P_{20}$ (referring to FIG. 6) that is the X-ray image following aligning the locations acquired by aligning the X-ray images (original images) $P_{10}$ so that each feature point coincides with each display-location. The correction images $P_{20}$ that are generated in series are sent to the image memory storage 43. In addition, in the case of fluoroscopy, the correction images $P_{20}$ are sent to the monitor 44 to display the images in real time without being sent to be stored in the image memory storage 43. Needless to say, given it is not problematic even when the time-lag takes place somewhat, the correction images $P_{20}$ can be sent to the image memory storage 43 even upon fluoroscopy.

The correction images $P_{20}$ that are generated in series are written and stored in the memory storage 43. The correction images $P_{20}$ that are stored in the image memory storage 43 are read out and sent to the monitor 44 to display each time-series correction image $P_{20}$ to display on the monitor 44 one by one. In addition, referring to FIG. 2, the X-ray images (original images) $P_{10}$ and the correction images $P_{20}$ are stored in the same image memory storage 43, but the X-ray images (original images) $P_{10}$ and the correction images $P_{20}$ can be stored separately in the different image memory storage.

The display control circuit 35 that controls the correction images $P_{20}$ to be displayed in series on the monitor 44. In such a way, the correction images $P_{20}$ are displayed on the monitor as a video.

The X-ray image generation circuit 31, the feature point location acquisition circuit 32, the feature point display-location determination circuit 33 and the correction image generation circuit 34 comprise a central processing unit (CPU) and so forth as well as the controller 42. The display control circuit comprise a graphics processing unit (GPU) and so forth that are applied to an image processing. The X-ray image generation circuit 31, the feature point location acquisition circuit 32, the feature point display-location determination circuit 33 and the correction image generation circuit 34 comprise a central processing unit (CPU) and so forth as well as the controller 42.

Figure 3:
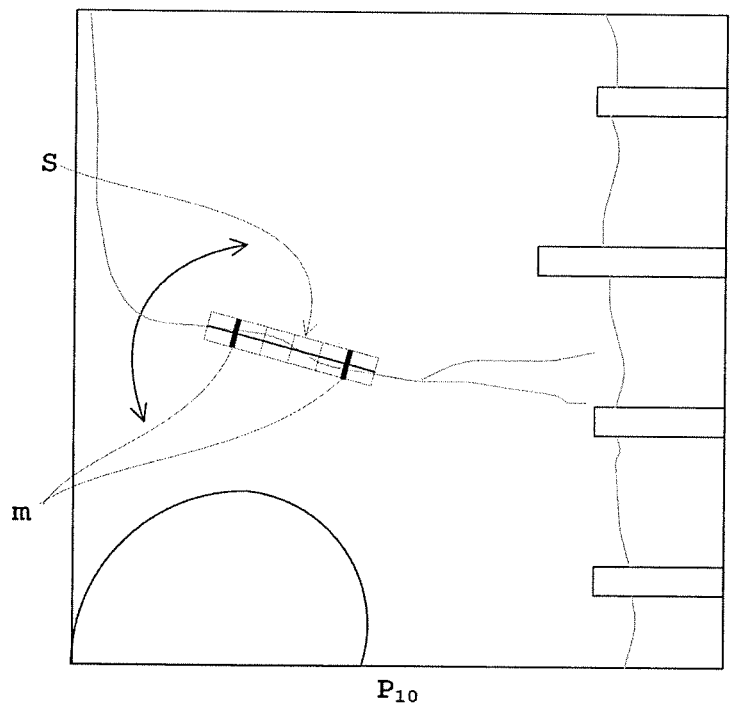
FIG. 3 is a schematic view illustrating a PTCA image that is obtained on the percutaneous transluminal coronary angioplasty.
Figure 4:
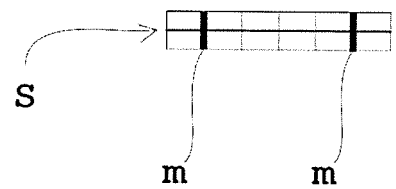
FIG. 4 is a magnified view illustrating a balloon marker and a stent.
Figure 5A:
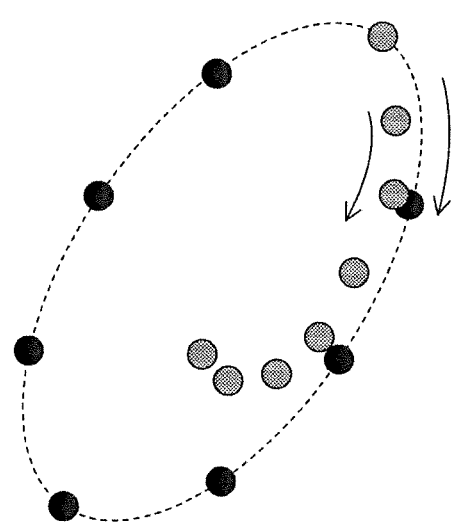
FIGS. 5A, 5B are schematic diagrams illustrating movements of the marker and a display-location according to the aspect of the Embodiment 1.
Figure 5B:
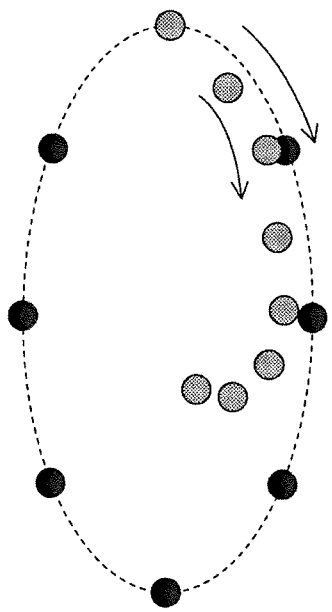
Figure 6:
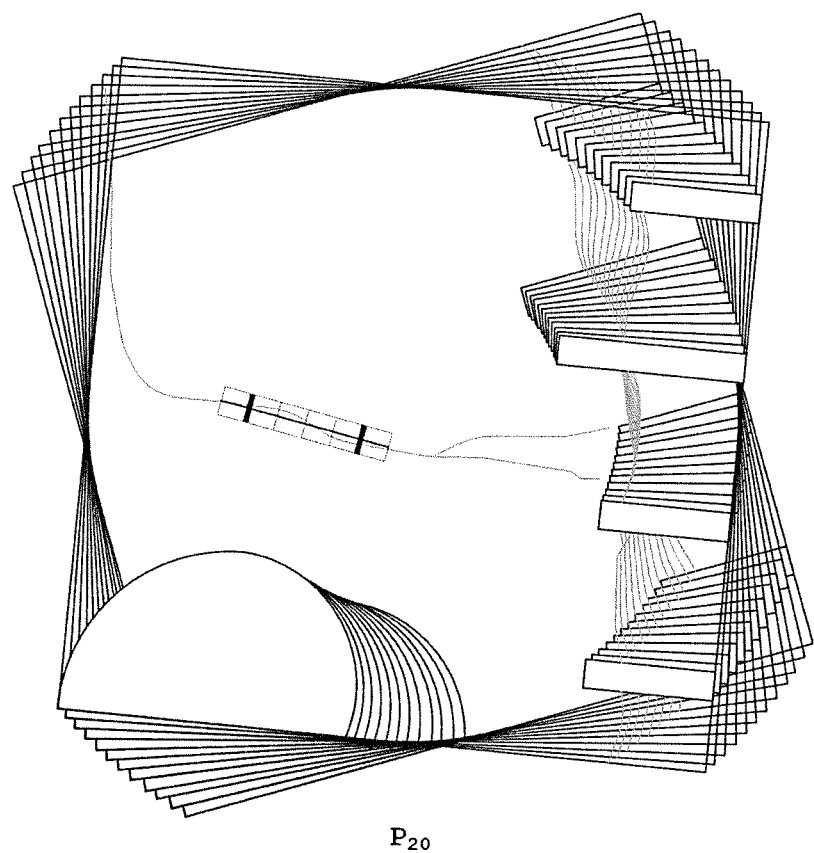
FIG. 6 is a schematic view illustrating an example of the correction image subjected to an alignment.
Figure 7:
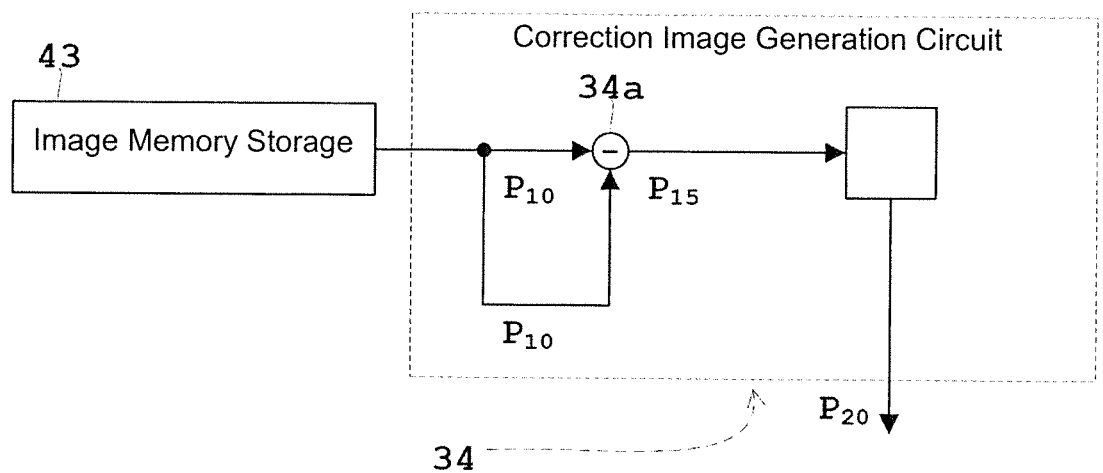
FIG. 7 is a block diagram illustrating a periphery of a correction image generation circuit when aligning background difference images.
Figure 8:
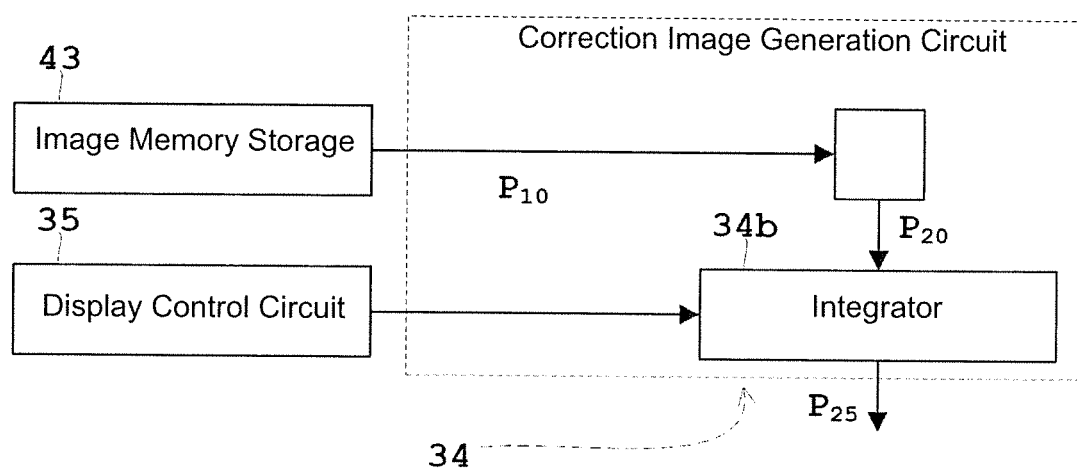
FIG. 8 is a block diagram illustrating the periphery of the correction image generation circuit when executing a time integration relative to the time-series correction images.

Next, referring to FIG. 1, FIG. 2 and FIG. 3-FIG. 8, the inventors set forth a series of imaging and image processing. FIG. 3 is a schematic view illustrating a PTCA image that is obtained on the percutaneous transluminal coronary angioplasty, FIG. 4 is a magnified view illustrating a balloon marker and a stent, FIGS. 5A, 5B are schematic diagrams illustrating movements of the marker and a display-location according to the aspect of the Embodiment 1, FIG. 6 is a schematic view illustrating an example of the correction image subjected to an alignment, FIG. 7 is a block diagram illustrating a periphery of a correction image generation circuit when aligning background difference images, and FIG. 8 is a block diagram illustrating the periphery of the correction image generation circuit when executing a time integration relative to the time-series correction images.

First, referring to FIG. 1, the CVS apparatus having the C-arm 23 is applied to a video-imaging of the subject M (referring to FIG. 1) who is a patient. The X-ray image generation circuit 31 (referring to FIG. 2) generates the X-ray image (original image) $P_{10}$ (referring to FIG. 3) that is projected on the detector surface of the FPD 25 (referring to FIG. 1, FIG. 2). In addition, the generated original image $P_{10}$ is a PTCA image that is obtained by the percutaneous transluminal coronary angioplasty (PTCA) and looks like an image referring to FIG. 3.

Referring to FIG. 3, the original image $P_{10}$ incorporates the stent S (referring to FIG. 4) that moves materially as one with two balloon markers m (referring to FIG. 4), for example, the balloon marker m and the stent S are moving based on the beat and the breathing in the direction indicated by the arrow in FIG. 3. Referring to FIG. 4, the balloon having a high-contrast can be easily recognized and on the other hand, the stent S has a low-contrast and fine structure, so that given moving vigorously, a fine part is particularly difficult to be observed, Next, the feature point location acquisition circuit 32 (referring to FIG. 2) extracts the location of each balloon marker m in the original image $P_{10}$ as the location of the feature point using the known method disclosed in such as the cited Patent Document and so forth. In addition, the specific method to extract the feature point is publicly known, so that the inventors skip the detail thereof. Each locational information (i.e., feature point) every frame that is extracted is written in the RAM and so forth as the time-series information and stored therein. In such a case, two markers of each frame must be correspondingly distinguished with each other.

Therefore, utilizing the fact that the upper left of the screen generally denotes the periphery of the coronary artery and the lower right denotes the distant region, the upper left of the screen is specified as the reference and the distance (i.e., the number of pixels) between the reference and the marker is calculated and the one having the shorter distance (less pixels) is specified as the marker 1 and the other having the longer distance (more pixels) is specified as the marker 2, correspondingly. A method for corresponding markers can use the shape when the shapes are different one another, or the other anatomical information can be applied thereto also. In addition, the feature point being extracted is not mandatory in one together with the target object and may be one moving substantially together with the target object. In addition, the CPU, such as the feature point location acquisition circuit 32, can automatically extract all markers, or the user manually designates an adequate marker through the input circuit 41 (referring to FIG. 2).

Next, referring to FIGS. 5A, 5B (two markers in FIGs.), the feature point display-location determination circuit 33 (referring to FIG. 2) calculates an average of the locations of each marker (refer to the black circle) and determines the display-location of each marker (refer to the gray circle). Specifically, the display-location of each marker is the original location of the marker per se relative to the display-location of the first frame (initial frame), is the middle point between the marker of the first frame and the marker of the second frame relative to the display-location of the second frame, and is the average between the marker of the first frame and the marker of the third frame relative to the third frame, which is approximately near the marker of the second frame, and then after, the average of each marker is acquired as the display-location.

Accordingly, movement of the display-location of each marker becomes gradually slow as indicated by the gray circle referring to FIGS. 5A, 5B and when movement due to the heart beat is over one cycle, the display-location converges to the proximity of the average location. More or less, the movement is much less, the display-location suspends to be updated (i.e., the display-location is acquired in series) and the display-location can be fixed. Instead of the average value, the median value can be applied also, and an adequate location can be obtained even when the abnormal coordinate (pixel location) is included due to the erroneous extraction of the feature point.

Next, referring to FIG. 6, the correction image generation circuit 34 (referring to FIG. 2) generates the location aligned X-ray image acquired by aligning the original images $P_{10}$ in real-time as the correction image $P_{20}$ so that each feature point (here, each marker) coincides with each display-location. The stent is projected in the two-dimensional image despite three-dimensional movement per se, so that the stent translates, rotates and moves in the image and in addition, the interval between the markers varies as short and long depending on the projection angle, and the stent is incorporated as if the length thereof varies. Therefore, in addition of translation and rotation-movement, magnifying or reducing along the axis of the stent is executed to fit such an interval so that the location of each marker overlaps. Accordingly, the target object is at all times fixed to the average location, the average direction and the average size at the end.

In addition, with regard to the target image for aligning, the background difference image $P_{15}$ (referring to FIG. 7) can be applied instead of the original image $P_{10}$. Specifically, referring to FIG. 7, the correction image generation circuit 34 further comprises a subtractor 34a that executes a time subtraction on the time-series X-ray images (original image) $P_{10}$ and generates a background difference image $P_{15}$ in series by such a time subtraction. And the correction image generation circuit 34 sequentially generates such time-series correction images $P_{20}$ as the correction image $P_{20}$ that is the location aligned background difference image obtained by aligning locations of such background different images $P_{15}$. The subtractor 34a is connected with the image memory storage 43. In addition, a delay circuit (not shown in FIG.) can be installed between the image memory storage 43 and the subtractor 34a to delay the original image $P_{10}$ of the past frame by the delay circuit. The subtractor 34a comprises an operational amplifier and a resistance. The subtractor 34a corresponds to the background difference image generation circuit of the present invention.

The subtractor 34a can erase the part not moving in the background by subtracting between the original image $P_{10}$ of the present frame and the original image $P_{10}$ i.e., carrying out the time subtraction relative to the original image $P_{10}$. In addition, with regard to the subtraction, the subtraction can be carried out using the average of the images of a plurality of past frames as the original image $P_{10}$ of the past frame. Further, when the subtraction is carried out using the average of the images of a plurality of past frames as the original image $P_{10}$ of the past frame, an additional effect, in which the statistical noise decreases, is expected. In addition, it is preferable that the subtraction is carried out using the just one previous frame of the original image $P_{10}$ of the present frame as the original image $P_{10}$ of the past frame. Regardless average or singularity, given the subtraction is carried out using the just previous frame as the original image $P_{10}$ of the past frame, the movement due to such as breathing that is slower than the movement of the X-ray irradiation rate can be excluded by such a subtraction.

In addition, the time integration can be carried out relative to the correction image $P_{20}$ following alignment. Specifically, referring to FIG. 8, the correction image generation circuit 34 further comprises an integrator 34b that executes a time integration on the time-series X-ray images (original image) $P_{20}$ and generates a time integration correction image $P_{25}$ in series by such a time integration. The display control circuit 35 controls the time integration correction images $P_{25}$ to be displayed in series. In such a way, the time integration correction images $P_{25}$ are displayed on the monitor 44 (referring to FIG. 2). In addition, the time integration correction image $P_{25}$ can be also once stored in the image memory storage 43 and then, controlled to be displayed on the monitor 44. The integrator 34b comprises an operational amplifier and a condenser (capacitance). In addition, temporal filtering or recursive filters (recursive calculation) relative to the correction image $P_{20}$ of the past frame can be carried out on the correction image $P_{20}$ following alignment. The integrator 34b corresponds to the time integration correction image circuit of the present invention.

At the end, the display control circuit 35 controls the time-series correction image $P_{20}$ (time integration correction image $P_{25}$ in the case of the time integration referring to FIG. 8) to be displayed on the display 44 in real time. Here, the inventors set forth a real-time display such as fluoroscopy, but even in the case of video replay, the video display is the same as the real-time display except that each image is stored in the image memory storage 43 and read out when replayed, so that the inventors skip the specific explanation relative to the video replay.

The X-ray apparatus according to the aspect of the present Embodiment 1, determines the display-location of respective feature points (markers) of such frames in-series based on the locations of the time-series feature points (of a plurality of frames), so that such an X-ray apparatus can display the moving target object (blood vessel) that is set up to have an adequate location, direction and size thereof. In addition, a plurality of feature points is extracted, so that the information of the direction and size of the target object (e.g., blood vessel) is maintained, and it is effectively distinguishable whether the target object (e.g., blood vessel) is proximal or distant and the length of the device (e.g., stent) can be understood intuitively from the image. In addition, the alignment is executed using both the locations of a plurality of feature points (markers) and a plurality of display-locations, so that the correction image per se that are displayed at the end can be set up so as to have the accurate location and direction.

In addition, according to the aspect of the present Embodiment 1, the feature points (markers) can be extracted a plurality of times relative to respective images that are generated in series. Needless to say, the feature point (marker) can be extracted just once also.

According to the aspect of the present Embodiment 1, it is preferable that a predetermined location is calculated based on the location of each time-series feature point (marker) and the calculated predetermined locations are determined in series as respective locations of a plurality of feature points (markers) to be displayed. The display-location of the feature point (marker) can be determined adequately and automatically based on such a calculation. Particularly, when the locations of respective time-series feature points (respective markers) are averaged, the movement of the display-location becomes gradually slow as described referring to FIGS. 5A, 5B and converges to the average location of respective feature points due to the movement (e.g., beat) at the end. Therefore, the moving target object (blood vessel) can be fixed to have the average location, the average direction and the average size and then displayed at the end. In addition, the process to reach the end is gradually, slowly and naturally proceeds without an unnatural sensation. In addition, given the median value of the locations of the respective time-series feature points (respective markers) is used, the location of the feature point is further strong despite missing the frame due to the mistake relative to the extraction of the feature point (marker).

In addition, when the locations of respective time-series feature points are averaged, the feature point (marker) is fixed to the predetermined location from the initial frame, the change of rotation and size of such a feature point (marker) as the center thereof becomes gradually slow, and then as set forth above, the target object (blood vessel) can be displayed while fixing the target object to the average direction and average size at the end. Regardless the location of the target object (blood vessel) on the screen, the display can display the feature point in an adequate location. In addition, when averaging the locations of the respective time-series feature points (markers) or using the median value of the respective time-series feature points (respective markers), the respective display-locations of the feature points (markers) are specified as the average of locations of the plurality of feature points (markers) or the median value thereof, so that the adequate location of the target object (blood vessel) can be displayed in the center of the display (screen) at the end.

In addition, according to the aspect of the present Embodiment 1, as set forth referring to FIG. 7, it is preferable that the correction image generation means (correction image generation circuit 34 of the present Embodiment 1) further comprises the background difference image generation means (subtractor 34a of the present Embodiment 1) that executes a time subtraction on the time-series radiographs (original image $P_{10}$ of each Embodiment) and generates background difference images in series by such a time subtraction, and the correction image generation means (correction image generation circuit 34) that sequentially generates such time-series correction images as the correction image that is a location aligned background difference image obtained by aligning locations of the background different images. Specifically, the background subtraction by the time subtraction is executed prior to the alignment of the target objects (blood vessel), so that the background subtraction image, from which the background having less movement is erased instead of the original image, can be displayed. The background difference image in which the background is disappeared in advance is displayed, so that worsening of the visibility of the target region and discomforting due to movement of the background not subjected to the alignment do not take place.

In addition, according to the aspect of the present Embodiment 1, as set forth referring to FIG. 8, it is preferable that the correction image generation means (correction image generation circuit 34) further comprises a time integration correction image means (integrator 34b according to the aspect of the present Embodiment 1) that executes a time integration on the time-series correction image and generates a time integration correction image in series by such a time integration, and that the display control means (display control circuit 35 according to the aspect of the present Embodiment 1) controls displaying such a time integration correction image in series. Specifically, the time integration is executed following aligning the locations of the target object (blood vessel), so that noise are cut and the visibility of the fine target object having low-contrast can be improved. The time integration of the background without aligning is executed, so that worsening of the visibility of the target region and discomforting due to movement of the background without aligning can be alleviated.

Embodiment 2

Figure 9:
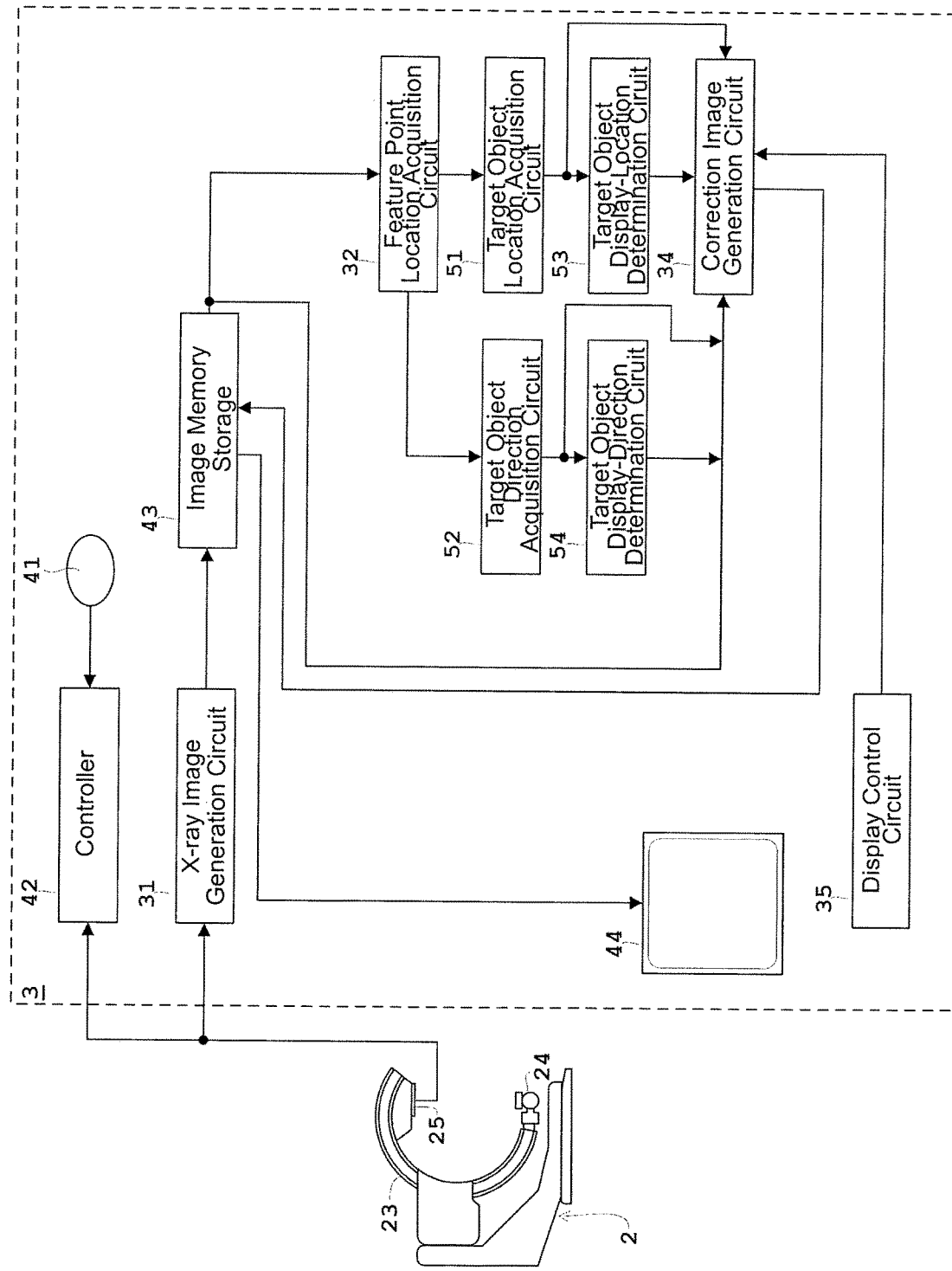
FIG. 9 is a block diagram illustrating the image processing system of the X-ray apparatus according to the aspect of the Embodiment 2.

Next, referring to FIGs, the inventors set forth the Embodiment 2 of the present invention. FIG. 9 is a block diagram illustrating the image processing system of the X-ray apparatus according to the aspect of the Embodiment 2. The same element as the above Embodiment 1 is indicated by the same sign and the illustration thereof is omitted.

Referring to FIG. 9, the image processing system 3, according to the aspect of the present Embodiment 2, comprises the X-ray image generation circuit 31 as well as the Embodiment 1 set forth above, the feature point location acquisition circuit 32, the correction image generation circuit 34 and the display control circuit 35. According to the aspect of the Embodiment 1 set forth above, the feature point display-location determination circuit 33 (referring to FIG. 2) comprises the image processing system 3 and in contrast, according to the aspect of the present Embodiment 2, referring to FIG. 9, the feature point display-location determination circuit 33 comprises a target object location acquisition circuit 51 that determines locations of the target objects based on the location of a plurality of feature points every same frame extracted in series and acquires the location of the time-series target object in series, a target object direction acquisition circuit 52 that determines a direction of the target object based on locations of said plurality of feature points every same frame extracted in series and acquires time-series directions of the target object in series, a target object display-location determination circuit 53 that determines in series a display-location of the target object to be displayed based on locations of the time-series target object acquired in series, and a target object display-direction determination circuit 54 that determines in series a display-direction of the target object to be displayed based on the direction of the time-series target object acquired in series.

Even according to the aspect of the present Embodiment 2, the X-ray image generation circuit 31 corresponds to the radiography generation means of the present invention, the feature point acquisition circuit 32 and the input circuit 41, set forth later, correspond to the feature point acquisition means of the present invention, the correction image generation circuit 34 corresponds to the correction image generation means of the present invention, and the display control circuit 35 corresponds to the display control means of the present invention. In addition, according to the aspect of the present Embodiment 2, the target object location acquisition circuit 51 corresponds to the target object location acquisition means of the present invention, the target object direction acquisition circuit 52 corresponds to the target object direction acquisition means of the present invention, the target object display-location determination circuit 53 corresponds to the target object display-location determination means of the present invention, and the target object display-direction determination circuit 54 corresponds to the target object display-direction determination means of the present invention.

Other than the above, the image processing system 3 comprises an input circuit 41, a controller 42, an image memory storage 43 and a monitor 44 as well as the Embodiment 1 as set forth above. In addition, the target object location acquisition circuit 51, the target object direction acquisition circuit 52, the target object display-location determination circuit 53 and the target object display-direction circuit 54 comprise a central processing unit (CPU) and so forth as well as the controller 42. In addition, the target object location acquisition circuit 51, the target object direction acquisition circuit 52, the target object display-location determination circuit 53 and the target object display-direction determination circuit 54 comprise a GPU.

As well as the Embodiment 1 as set forth above, the X-ray image generation circuit 31 sequentially generates time-series X-ray images (original images) $P_{10}$ (referring to FIG. 3) based on X-ray imaging in which X-rays are irradiated toward the subject M (referring to FIG. 1) and the X-rays transmitting through the subject M is detected (by FPD 25). The X-ray images (original images) $P_{10}$ generated in series are written and stored in the memory storage 43. The X-ray images (original images) $P_{10}$ stored in the image memory storage 43 are read out and sent to the feature point location acquisition circuit 32 and the correction image generation circuit 34 to extract the location of the feature point and acquire or align therefor.

As well as the Embodiment 1 as set forth above, the feature point location acquisition circuit 32 extracts locations of a plurality of feature points that a predetermined target object possesses based on such X-ray images (original images) $P_{10}$ generated in series and acquires time-series locations of the plurality of feature points in series. According to the aspect of the present Embodiment 2, a plurality of the feature points extracted in series is sent to the target object acquisition circuit 51 and the target object direction acquisition circuit 52.

Figure 10:
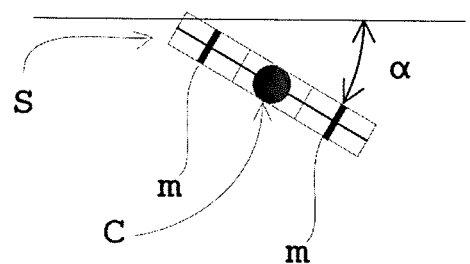
FIG. 10 is a schematic view illustrating the location of the stent and the angle thereof.

The target object location acquisition circuit 51 that determines the location of the target object based on the locations of the plurality of feature points every same frame extracted in series and acquires time-series locations of the target object in series. According to the aspect of the present Embodiment 2, the target object acquisition circuit 51 calculates a predetermined location based on the locations of a plurality of feature points every same frame and determines that such calculated predetermined locations are the locations of the target object in series. The specific calculation is not particularly limited, but the average value of the plurality of the feature points every same frame or the median value thereof is determined in series as the locations of the target object. Referring to FIG. 10, the inventors set forth later the location of the target object (e.g., stent) obtained by the calculation. The location of the target object is sent to the feature point display-location determination circuit 53 and the correction image generation circuit 34.

The target object direction acquisition circuit 52 determines the direction of the target object based on the locations of the plurality of feature points every same frame extracted in series and acquires time-series directions of the target object in series. According to the aspect of the present Embodiment 2, a predetermined direction is calculated based on the direction of a regression line relative to the plurality of feature points every same frame and such a calculated predetermined direction is determined as a direction of the target object in series. Referring to FIG. 10, the inventors set forth later the angle of the target object (stent) obtained by the calculation. The direction of the target object is sent to the target object display-direction determination circuit 54 and the correction image generation circuit 34.

The target object display-location determination circuit 53 that sequentially in series a display-location of the target object to be displayed based on locations of the time-series target object acquired in series. According to the aspect of the present Embodiment 2, the predetermined location of the target object is calculated based on the time-series locations acquired in series, and the calculated predetermined location is determined as the display-location of the target object in series. The specific calculation is not particularly limited, but the average value of the locations of the time-series feature point or the median value thereof is determined in series as the respective display-locations of the target object. Other than the above, as well as the Embodiment 1 set forth above, for example, the mode value may be determined as the respective display-locations of the target object in series. The inventors set forth the specific movements of the display-locations of the target object (middle point of the marker) and display-locations obtained by the above calculation later referring to FIGS. 11A-11C. Each display-location is sent to the correction image generation circuit 34.

The target object display-direction determination circuit 54 that sequentially determines display-direction of the target object to be displayed based on directions of the time-series target object acquired in series. According to the aspect of the present Embodiment 2, the predetermined direction of the target object is calculated based on the time-series directions of the target object acquired in series, and the calculated predetermined direction is determined as the display-direction of the target object in series. The specific calculation is not particularly limited, but the average value of the angles of the time-series target object or the median value thereof is determined in series as the respective display-directions of the target object. Other than the above, as well as the target object display-location determination circuit 53, the Embodiment 2, for example, the mode value may be determined as the respective display-directions of the target object in series. The inventors set forth the location (median of the marker) of the target object and display-directions obtained by the above calculation later referring to FIGS. 11A-11C. Each display-direction is sent to the correction image generation circuit 34.

The correction image generation circuit 34 that sequentially generates time-series correction images $P_{20}$ as the correction image $P_{20}$ (referring to FIG. 6) that is the X-ray image following aligning the locations acquired by aligning the X-ray images (original images) $P_{10}$ so that each location of the target object point coincides with each display-location and each direction of the target object coincides with each display-direction. The correction images $P_{20}$ that are generated in series are written and stored in the memory storage 43. The correction images $P_{20}$ that are stored in the image memory storage 43 are read out and sent to the monitor 44 to display each time-series correction image $P_{20}$ on the monitor 44 one by one.

As well as the aspect of the Embodiment 1 set forth above, the display control circuit 35 controls the correction images $P_{20}$ to be displayed on the monitor 44 in series, so that the time-series correction images $P_{20}$ are displayed as a video on the monitor 44.

Figure 11:
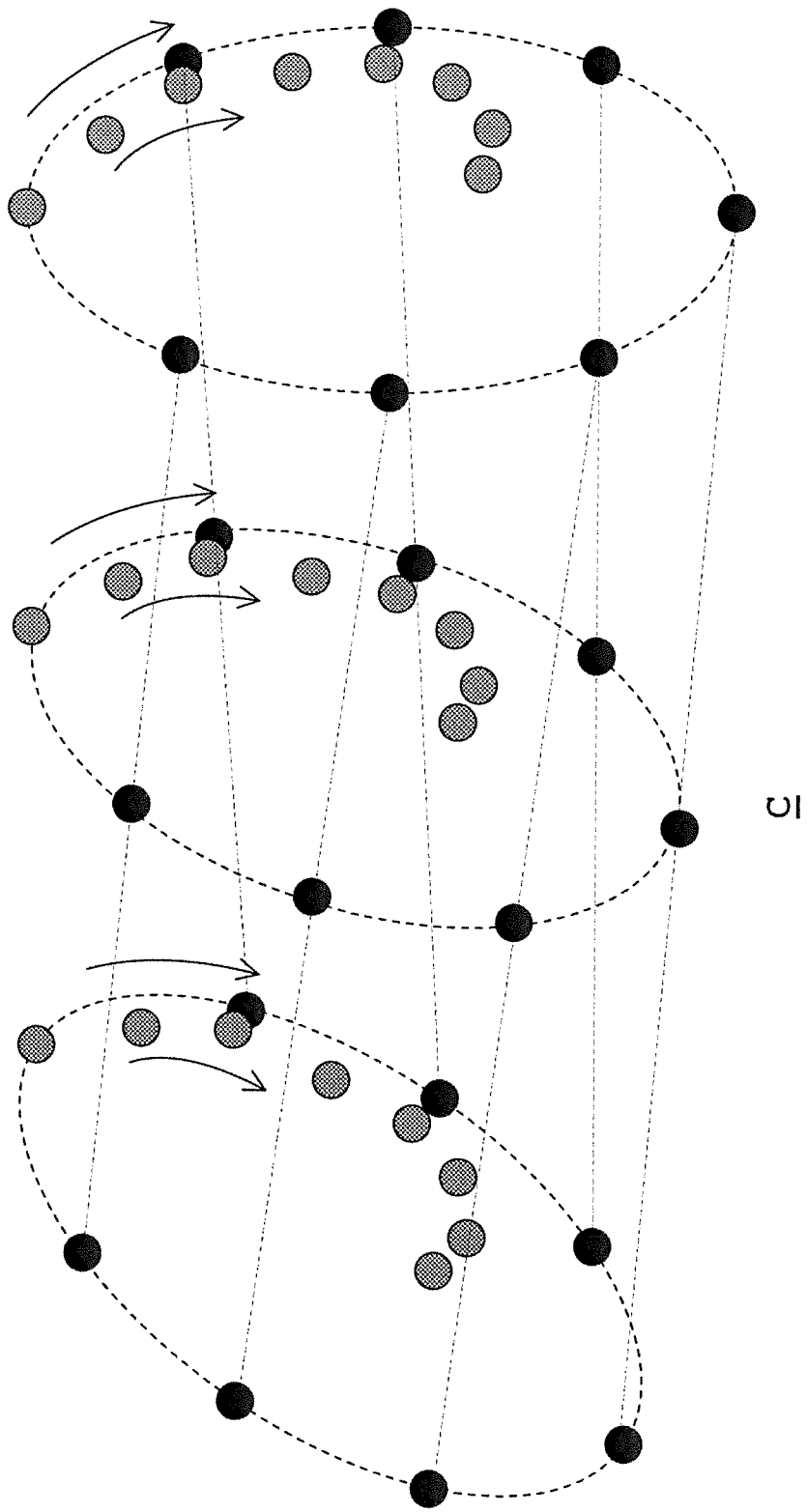
FIGS. 11A, 11B, 11C are schematic diagrams illustrating movements of the middle point of the marker and the display-location according to the aspect of the Embodiment 2.

Next, referring to FIG. 1, FIG. 3 and FIG. 6-FIG. 8 according to the Embodiment 1 set forth above and FIG. 10, FIGS. 11A-11C as well as FIG. 9 according to the Embodiment 2, the inventors set forth a series of imagings and image processings. FIG. 10 is a schematic view illustrating the location of the stent and the angle thereof, and FIGS. 11A-11C is a schematic diagram illustrating movements of the middle point of the marker and the display-location according to the aspect of the Embodiment 2. In addition, only the end result of the display-direction is illustrated in FIGS. 11A-11C.

As well as the Embodiment 1 set forth above, first, referring to FIG. 1, the CVS apparatus having the C-arm 23 is applied to video-imaging of the subject M (referring to FIG. 1) who is a patient. The X-ray image generation circuit 31 (referring to FIG. 9) generates the X-ray image (original image) $P_{10}$ (referring to FIG. 3) that is projected on the detector surface of the FPD 25 (referring to FIG. 1, FIG. 9), i.e., such an original image $P_{10}$ is the PTCA image obtained by PTCA (percutaneous transluminal coronary angioplasty) as the denoted image in FIG. 3.

As well as the Embodiment 1 set forth above, the feature point location acquisition circuit 32 (referring to FIG. 9) extracts the location of each balloon marker m in the original image $P_{10}$ as the location of the feature point using the known method disclosed in such as the cited Patent Document and so forth.

Then, referring to FIG. 10, the target object location acquisition circuit 51 (referring to FIG. 9) calculates the average of locations of the two markers m. Referring to FIG. 10, the number of the markers m is 2, so that the average of the two markers m is the median C between the locations of the two markers m. Such a median C corresponds to the location denoting the stent S. Needless to say, the number of the marker can be more than three and the target object location acquisition circuit 51 can calculate the average value of a plurality (more than three) of locations of the marker (i.e., locations of the feature point).

On the other hand, referring to FIG. 10, the target object direction acquisition circuit 52 (referring to FIG. 9) calculates the angle α of the regression line relative to the two markers m. Referring to FIG. 10, the number of the markers m is 2, so that the regression line connecting two markers m is the straight line connecting two markers m. The angle α of such a line corresponds to the direction of the stent.

Needless to say, the number of the marker can be more than three and the target object direction acquisition circuit 52 can acquire the regression line relative to a plurality (more than three) of the markers (i.e., feature points). When the regression line relative to more than three feature points is acquired, a known method such as a least-square method and so forth can be applied.

In addition, referring to FIG. 10, the angle α is the angle between the pixel-line in the horizontal direction and the straight line connecting the two markers m, but the angle of the straight line can be the angle between the pixel-line in the vertical direction and the straight line connecting two markers m. In addition, the direction of the target object (i.e., stent) that the target object direction acquisition circuit 52 provides is not limited to the angle made of the straight lines referring to FIG. 10 and can be a vector relative to the other coordinate as the one coordinate of two markers m is the reference.

The median C and the angle α that the target object location acquisition circuit 51 and the target object direction acquisition circuit 52 provide every frame are written and stored in the memory medium such as a RAM as the time-series information. As set forth referring to the Embodiment 1 set forth above, in such a case, two markers of each frame must be correspondingly distinguished with each other.

Now, as set forth according to the aspect of the Embodiment 1, utilizing the fact that the upper left of the screen generally denotes the periphery of the coronary artery and the lower right denotes the distant region, the upper left of the screen is specified as the reference and the distance between the reference and the marker is calculated and the one having the shorter distance is specified as the marker 1 and the other having the longer distance (more pixels) is specified as the marker 2, correspondingly. According to the aspect of the present Embodiment 2, the user also manually designates an adequate marker through the input circuit 41 (referring to FIG. 2).

Next, referring to FIGS. 11A-11C (two markers in FIGs.), the target object display-location determination circuit 53 (referring to FIG. 9) calculates an average of the locations of time-series medians C (refer to the black circle in FIGS. 11A-11C) and specifies such an average as the display-location of the stent (refer to the gray circle in FIGS. 11A-11C). In addition, the target object display-angle determination circuit 54 (referring to FIG. 9) calculates the average of the time-series angles and specifies such an average as the display-direction of the stent.

Accordingly, movement of the display-location of the stent and the display-direction thereof becomes gradually slow as indicated by the gray circle referring to FIGS. 11A-11C compared to the actual movement of the stent and when movement due to the heart beat is over one cycle, the display-location and the display-direction converge to the proximity of the average location and the average direction. More or less, the movement is much less, the display-location and the display-direction suspend to be updated (i.e., the display-location and the display-direction are acquired in series) and the display-location and the display-direction can be fixed. Instead of the average value, the median value can be applied also, and an adequate location can be obtained even when the abnormal coordinate (pixel location) is included due to the erroneous extraction of the feature point.

Next, the correction image generation circuit 34 (referring to FIG. 9) generates the aligned X-ray image acquired by aligning the original images $P_{10}$ in real-time as the correction image $P_{20}$ (referring to FIG. 6) so that the median of the marker coincides with the display-location and the direction of the stent coincides with the display-direction. In addition, differently from the Embodiment 1 set forth above, the size of the stent is not changed from the original image $P_{10}$ and just translation and rotation and movement take place. Therefore, the original image $P_{10}$ never deforms.

According to the aspect of the present Embodiment 2 as well as the Embodiment 1 set forth above, with regard to the target image for aligning, the background difference image $P_{15}$ (referring to FIG. 7) can be applied instead of the original image $P_{10}$. The background difference image $P_{15}$ is the same according to the aspect of the Embodiment 1 set forth above, so that the inventors skip the explanation therefor.

In addition, according to the aspect of the present Embodiment 2 as well as the Embodiment 1 set forth above, the time integration can be carried out relative to the correction image $P_{20}$ following alignment. The time integration correction images $P_{25}$ (referring to FIG. 8) obtained by time integration are displayed in series. The time integration image $P_{25}$ is the same according to the aspect of the Embodiment 1 set forth above, so that the inventors skip the explanation therefor.

At the end, the display control circuit 35 controls the time-series correction image $P_{20}$ (time integration correction image $P_{25}$ in the case of the time integration referring to FIG. 8) to be displayed on the display 44 in real time.

The X-ray apparatus according to the aspect of the present Embodiment 2, determines the respective display-locations and display-directions of the target object (e.g., stent) of such frames in-series based on the locations and directions of the time-series feature point (here, marker) (of a plurality of frames), so that such an X-ray apparatus can display the moving target object (stent) that is set up so as to have an adequate location and direction thereof. In addition, the direction of the target object (stent) is displayed under consideration of the direction of the target object (stent) based on a plurality of feature points (markers), so that even when the direction changes, the target object (stent) per se is not deformed and as a result, the form of the target object (stent) is never unnatural. In addition, as well as the Embodiment 1 set forth above, a plurality of feature points (markers) is extracted, so that the information of the direction and size of the target object (stent) is maintained, and it is effectively distinguishable whether the target object (e.g., blood vessel) is proximal or distant and the length of the device (e.g., stent) is understandable intuitively from the image. In addition, the alignment is executed using both the location and direction of the target object (here, the median of the markers and the direction of the marker), so that the correction image per se that are displayed at the end can be set up so as to have the accurate location and direction.

In summary, the alignments according to the aspect of the Embodiment 1 and the present Embodiment 2 as set forth above are different in the following aspects. According to the aspect of the Embodiment 1, movement, rotation (isotropic or anisotropic) magnifying, shrinking or deformation takes place. The device (e.g., stent) converges to an average location, an average angle and an average size (form). The size is also averageable, but negatively, anisotropic magnifying, shrinking and deformation likely result in proving an unnatural image. In addition, the calculation cost therefor is larger. According to the aspect of the Embodiment 2, movement and rotation take place. The device (e.g., stent) converges to an average location and an average angle. Even though the size is not averageable, no deformation takes place, so that the image is never unnatural. In addition, the actual change of the size is so small that it is not concerned at all. In addition, the calculation cost therefor is smaller.

According to the aspect of the present Embodiment 2, in the pre-step for determining the display-location of the target object (stent) and the display-direction thereof, the location and direction of the target object (stent) that are the bases of the display-location and display-direction of the target object can be determined based on the calculation set forth above. Specifically, a predetermined location is calculated based on locations of a plurality of feature points (markers), such a calculated location is acquired in series as a location of the target object (stent), the predetermined direction is calculated based on the direction of the regression line relative to the plurality of feature points (markers), and such a calculated predetermined direction is acquired in series as the direction of the target object (stent). For example, referring to FIG. 10, the median between two markers m is acquired as the location of the target object and the angle $\alpha$ relative to the straight lines connecting two markers m is acquired as the direction of the stent S, i.e., the direction of the target object. According to such a calculation, the location and direction of the target object can be determined adequately and automatically (as the median of the marker and the direction of the stent according to the aspect of the present Embodiment 2).

In addition, according to the aspect of the present Embodiment 2, it is preferable that the predetermined location and direction are calculated based on the time-series locations and directions (the median of the marker and the direction of the stent) acquired in series, and the calculated predetermined locations and directions are determined as the display-location and display-direction of the target object in series. According to such calculations, the display-location of the target object (stent) and the display-direction thereof can be determined adequately and automatically. Particularly, when averaging the locations and directions of the target object (stent), the movement of the display-location and the display-direction become gradually slow as set forth referring to FIGS. 11A-11C and converges to the average of movements of the location and direction of the target object (the median of the marker and the direction of the stent) due to such movements (e.g., beat) at the end. Therefore, the moving target object (stent) can be fixed to have the average location, the average direction and then, displayed at the end. In addition, the process to reach the end is gradually, slowly and naturally proceeds without an unnatural sensation. In addition, given the median value of the locations and directions (the median of the marker and the direction of the stent) of the time-series target object is used, the location of the feature point is further strong despite missing the frame due to the mistake relative to the extraction of the feature point.

In addition, when averaging the locations and directions (the median of the marker and the direction of the stent) of the time-series target object or using the median value of the location and directions (the median of the marker and the direction of the stent) of the target object, the display-location and display-direction of the target object is specified as the average of locations and directions (the median of the marker and the direction of the stent) of the time-series target objects or the median value thereof, so that the adequate location of the target object (stent) can be displayed in the center of the display (screen) and the target object (stent) can be set up in the adequate direction.

In addition, according to the aspect of the present Embodiment 2 as well as the Embodiment 1 set forth above referring to FIG. 7, it is preferable that the correction image generation circuit sequentially generates such time-series correction images as the correction image that is a location aligned background difference image obtained by aligning locations of the background different images. Specifically, the background subtraction by the time subtraction is executed prior to the alignment, so that the background difference image, from which the background having less movement is erased, can be displayed instead of the original image. The background difference image in which the background is disappeared in advance is displayed, so that worsening of the visibility of the target region and discomforting due to movement of the background not subjected to the alignment do not take place.

In addition, according to the aspect of the present Embodiment 2 as well as the Embodiment 1 as set forth above referring to FIG. 8, it is preferable that the correction image generation circuit executes a time integration on the time-series correction image and generates a time integration correction image in series by such a time integration. Specifically, the time integration is executed following aligning, so that noise is cut and the visibility of the fine target (stent) object can be improved with low-contrast. The time integration of the background without aligning is executed, so that worsening of the visibility of the target region and discomforting due to movement of the background without aligning can be alleviated.

The present invention is not limited to the aspect of the Embodiment set forth above and further another alternative Embodiment can be implemented as set forth below.

(1) According to the aspect of each Embodiment set forth above, the radiation is X-ray, but the other radiation than X-ray (e.g., radiofrequency wave and γ-ray) can be applied. For example, the present invention can be applied to the intervention therapy combining the nuclear medicine diagnosis and the angiographic technology.

(2) According to the aspect of each Embodiment set forth above, the radiation apparatus (X-ray apparatus in each Embodiment) is applied to a medical apparatus for a human subject, but the present invention can be also applied to an industrial apparatus such as non-destructive inspection system for the mounted substrate as the subject. Particularly, the present invention is useful for the subject having a dynamic object.

(3) According to the aspect of each Embodiment set forth above, the inventors set forth, for example, the PTCA (percutaneous transluminal coronary angioplasty), but the present invention can be applied to the intervention radiation medicine (IVR stands for intervention radiology) in general as the intervention therapy other than the PTCA. For example, with regard to IVR in general other than PTCA, the present invention is applicable for the catheter aortic valve replacement (TAVR). In the case of the TAVR, a metal frame of the prosthetic valve as the feature point relative to the prosthetic valve as the target object is applied, so that the prosthetic valve can be fixed and displayed. Therefore, when indwelling the prosthetic valve, the present invention facilitates the locational determination therefor. Reversely, the calcified lesion of the aortic valve can be used as the feature point, and in such case, the aortic valve to be indwelt is fixed and displayed.

Figure 12:
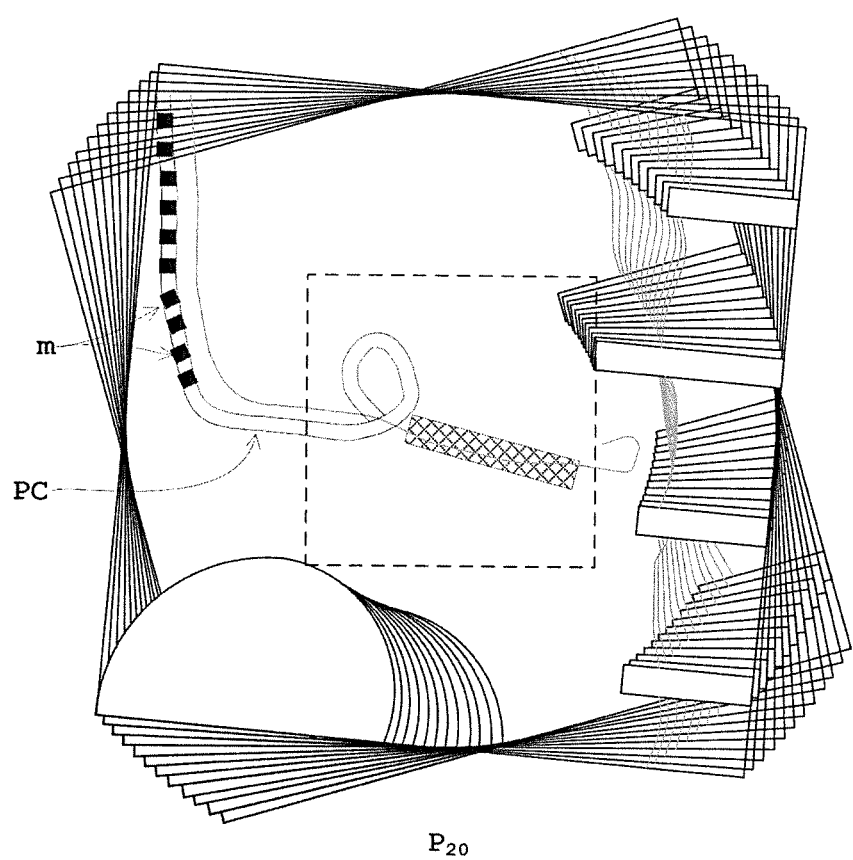
FIG. 12 is a schematic view illustrating an example of the correction image when applying to the transcatheter aortic valve replacement (TAVR).

(4) In addition, given no feature point corresponding to the target object is present, another marker different from the target object can be inserted into the region which moves substantially together with the target object as an integrated manner. For example, referring to FIG. 12, the marker m of a pigtail catheter (PC) that is inserted in a proximity of the prosthetic valve is such an example. In such a case, referring to FIG. 12, the proximity of the marker is not magnified and displayed, but instead, the center region (refer to the surrounded area by the broken line in FIG. 12) on the screen and so forth, in which the prosthetic valve or the aortic valve is predictively present, can be magnified and displayed. Needless to say, the location where the user such as a surgeon, who wants to magnify and display, can be designated.

(5) According to the aspect of the Embodiment 1 set forth above, the display-location of the feature point is automatically determined by calculating the predetermined location (the average value of the median value in the Embodiment 1) based on the time-series locations of each feature point, and according to the aspect of the Embodiment 2, the display-location and display-direction of the feature point are automatically determined by calculating the predetermined location based on the time-series locations (medians) and directions (angles) of the target object, but the display-location and the display-direction are not mandatorily required to be determined automatically. For example, according to the aspect of the Embodiment 1, the time-series locations of each feature point are displayed and then the user, such as a surgeon, can manually determine the display-location of the feature point based on the display-result, and also, according to the aspect of the Embodiment 2, the time-series locations (medians) and directions (angles) of each feature point are displayed and then the user, such as a surgeon, can manually determine the display-location and display-direction of the feature point based on the display-result.

(6) According to the aspect of the Embodiment 2 set forth above, the predetermined location (median) of the target object is automatically determined by calculating the predetermined location (median in the Embodiment 2) based on plurality of feature points, and the predetermined direction (angle in the Embodiment 2) is automatically determined based on the direction of the regression line relative to a plurality of feature points, but the location and direction of the target object are not mandatorily required to be determined automatically. For example, once the location of a plurality of feature points is displayed and then, the user, such as a surgeon, can manually determine the location and direction of the target object based on the display-result.

(7) The display control means (display control circuit 35 of each Embodiment) can magnify the predetermined area of the correction image and display such a magnified area in series. The predetermined area of the correction image is magnified and then, displayed in series, so that the target object can be observed in more detail. When the feature point and the target object are unified, the location of the target object is known, so that a proximity of the target object can be magnified and displayed. When the feature point and the target object are distant, the location where the target object is present is predicted from the relative location of the target object to the feature point is known, so that such a predicted location can be magnified and displayed. On the other hand, the user, such as a surgeon, designates the display area and magnifies the desired area and displays such an area.

Figure 13:
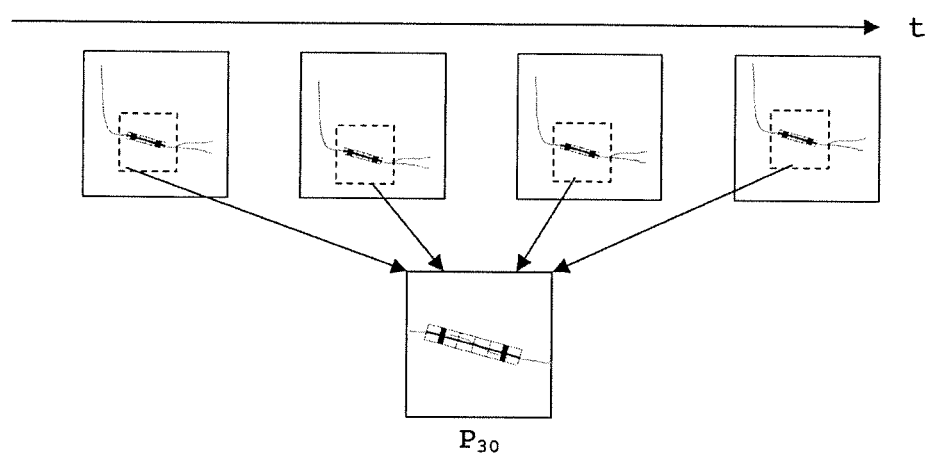
FIG. 13 is a schematic diagram illustrating a display aspect according to the aspect of the alternative Embodiment of the Embodiment 1.

(8) According to the aspect of the Embodiment 1 set forth above, the display control means (display control circuit 35 of the Embodiment 1) can display such a correction image so that the location of the target object relative to the correction image is always fixed to the center of the screen. For example, according to the aspect of the Embodiment 2, the median between two markers is acquired and specified as the location denoting the stent. Referring to FIG. 13, the location of the stent is fixed to the center of the screen while keeping the display-location of each marker relative to such a location of the stent. And then after, the correction image is displayed in real time (t denotes the time axis in FIG. 13, referring to the display-image P30 in FIG. 13) following the same alignment. In such a case, the location of the stent never shifts from the center and always fixed thereto, and then movement including only rotation or magnification and reduction takes place. As set forth referring to FIGS. 5A, 5B and FIGS. 11A, 11B, 11C, such a movement is averaged and fixed at the end. The stent is always in the center, so that such a stent can be magnified and displayed. In addition, the correction image can be juxtaposed with the original image at the same time.

Figure 14:
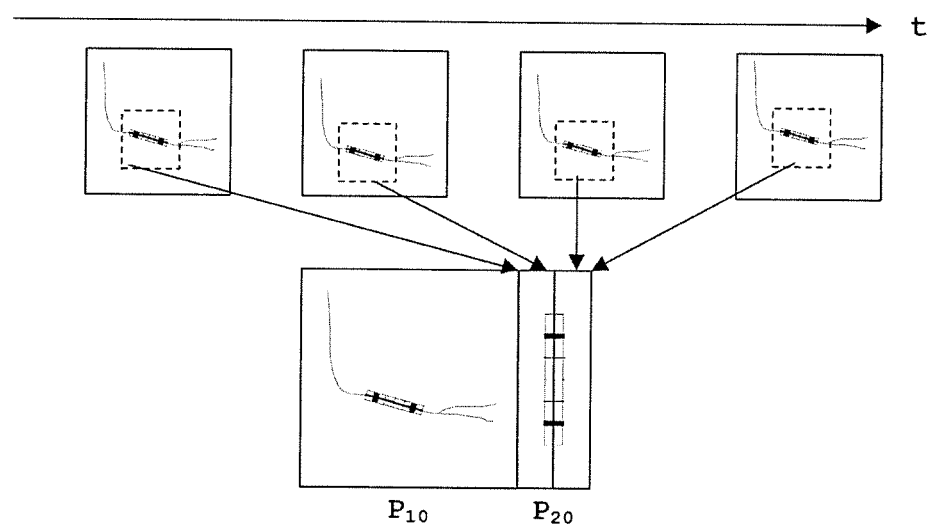
FIG. 14 is a schematic diagram illustrating a display aspect according to the aspect of the alternative Embodiment of the Embodiment 2.

(9) According to the aspect of the Embodiment 2 set forth above, referring to FIG. 14, the display control means (display control circuit 35 of the Embodiment 2) fixes the median of the two markers to the right side of the screen as the location denoting the stent and can fix and display the direction of the stent in the vertical direction. In such a case, the location of the stent in the right side of the screen neither shifts nor rotates, but is always fixed, and as a result, the movement thereof includes only magnification and reduction. Actually, the projection angle never varies largely, and it is deemed almost completely fixed. The stent is always in the right side, so that such a stent can be magnified and displayed. In addition, the stent can be displayed together with the original image at the same time (referring to the original image $P_{10}$ and the extracted correction image $P_{20}$ in FIG. 14).

Figure 15:
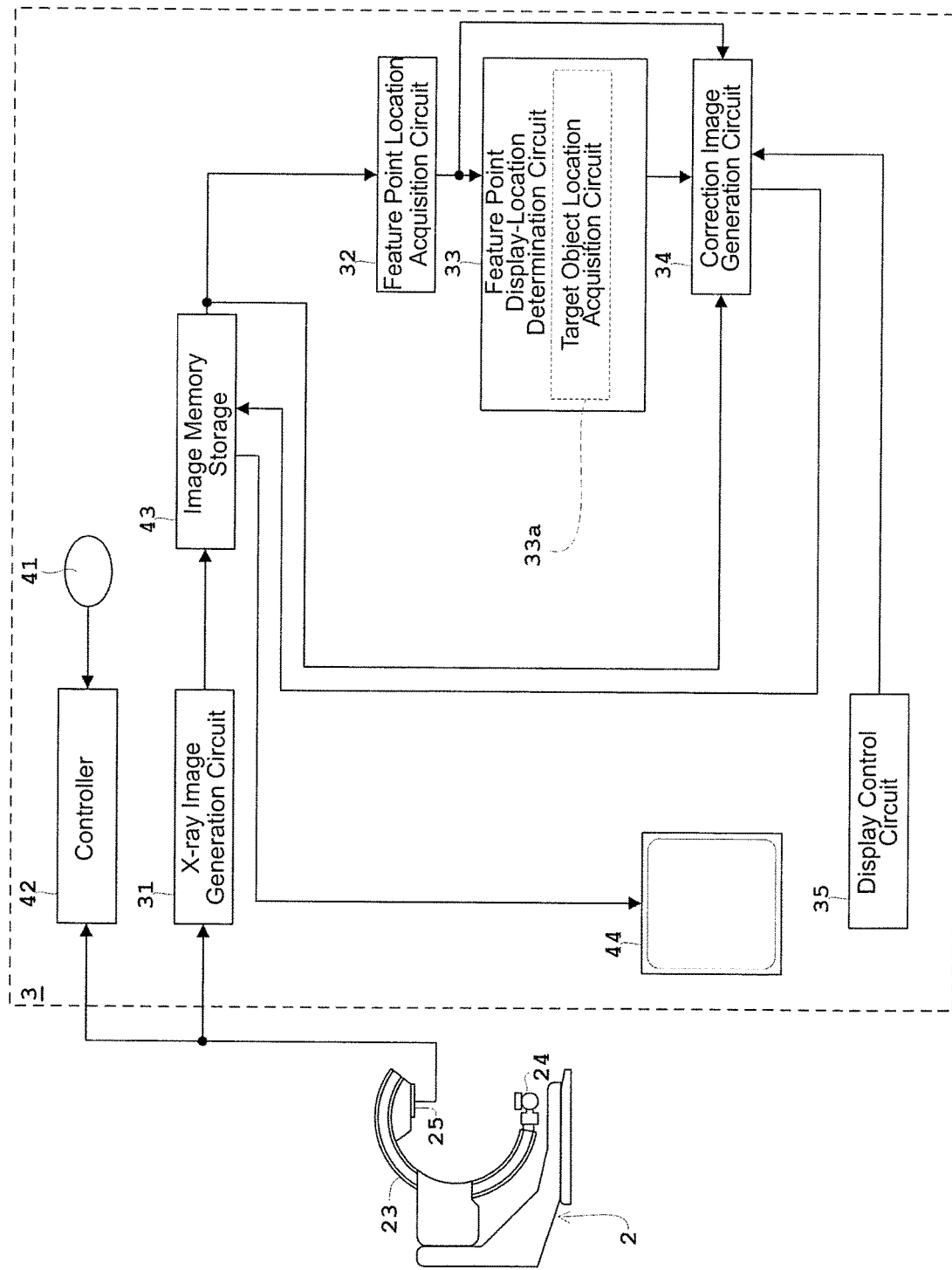
FIG. 15 is a block diagram illustrating the image processing system of the X-ray apparatus according to the aspect of another alternative Embodiment of the Embodiment 1.

(10) According to the aspect of the Embodiment 1 set forth above, referring to FIGS. 5A, 5B, when the feature point display-location determination means (feature point display-location determination circuit 33 according to the aspect of the Embodiment 1) determines the respective display-locations of the feature point in series, the respective display-locations are acquired independently each other, but the respective display-locations of the target object can be determined in series while keeping the relative location of the plurality of relative feature points to such locations of the target object following determination of the location (median C denoting the stent S referring to FIG. 10) of the target object based on the locations of the plurality of feature points as set forth above according to the aspect of the Embodiment 2. Specifically, referring to FIG. 15, the feature point display-location determination circuit 33 further comprises the target object location acquisition circuit 33a that determines the locations of the target object in series based on the locations of a plurality of feature points locations and acquires such determined locations of the target object in series. The feature point display-location determination circuit 33 determines in series respective locations of the plurality of feature points that should be displayed as the respective display-locations of the plurality of feature points so that the locations of the target object is a predetermined location while keeping the relative locations of the plurality of target object to the location of the target object. The target object acquisition circuit 33a comprises such as a central processing unit (CPU) and so forth, as well as the controller 42. In such a case, the moving target object is set up in the adequate location and direction while keeping the length and size of the target object. The target object location acquisition circuit 33a corresponds to the target object location acquisition means of the present invention.

(11) Particularly, the target object location acquisition circuit 33a comprises the central processing unit (CPU) and so forth, so that it is preferable that the predetermined location (e.g., average value or median value) is calculated based on the locations of a plurality of feature points and the calculated predetermined locations are acquired as the location of the target object. The display-location of the feature point of the target object can be determined adequately and automatically based on such a calculation. Needless to say, once the location of a plurality of feature points is displayed and then, the user such as a surgeon can manually determine the location of the target object based on the display-result.

REFERENCE OF SIGNS

31 X-ray image generation circuit
32 Feature point location acquisition circuit
33 Feature point display-location determination circuit
33a Target object location acquisition circuit
34 Correction image generation circuit
34a Subtractor
34b Integrator
35 Display control circuit
41 Input circuit
51 Target object location acquisition circuit
52 Target object direction acquisition circuit
53 Target object display-location determination circuit
54 Target object display-direction determination circuit
$P_{10}$ X-ray image (original image)
$P_{15}$ Background difference image
$P_{20}$ Correction image
$P_{25}$ Time integration correction image
M Subject Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A method of image processing, comprising the steps of:
acquiring a position of a feature point in a given object for each of a plurality of sequentially taken radiographic images;
identifying trajectories formed by the sequentially acquired feature points wherein the trajectories are formed by a series of feature points on sequential radiographic images;
determining a point on each radiographic image within a range of the identified trajectory; and
matching positions of the feature points on the radiation images to the determined point, thereby generating correction images.

2. A method of image processing, comprising the steps of:
acquiring a position of a feature point in a given object for each of a plurality of sequentially taken radiographic images;
identifying trajectories formed by the sequentially acquired feature points;
determining a point on each radiographic image within a range of the identified trajectory;
matching positions of the feature points on the radiation images to the determined point, thereby generating correction images;
wherein the step of determining a point on each radiographic image includes a step of determining an average of the positions of the plurality of feature points of the sequentially taken radiographic images; and
wherein the step of determining a point on each radiographic image includes a step of determining a point so that the average of the plurality of feature points maintains the positions of the plurality of feature points relative to the average of the positions of the plurality of feature points.

3. The method of image processing, according to claim 2, wherein:
the step of acquiring the position of the feature point includes a step of acquiring positions of a plurality of feature points.

4. The method of image processing, according to claim 2, wherein:
the step of determining a point on each radiographic image includes a step of calculating the point based on the position of each feature point in time series.

5. A method of image processing, comprising the steps of:
acquiring positions of a plurality of feature points of a given object for each of a plurality of sequentially taken radiation images;
obtaining an average of the positions of the plurality of feature points of the plurality of sequentially taken radiation images;
obtaining a direction of an object reflected in the radiation image, the obtainment being based on the positions of the plurality of feature points on the radiation image;
identifying a trajectory formed by the objects;
determining a point on the radiographic image within the range of the identified trajectory;
determining a direction of the object on an image based on the direction of the object sequentially obtained; and
matching the average of the positions to the determined point and matching the direction of the object to the determined direction thereby generating correction images.

6. The method of image processing, according to claim 5, wherein:
the step of obtaining the direction of the object includes a step of calculating the direction based on the direction of the regression line for the plural feature points.

7. The method of image processing, according to claim 5, wherein:
the step of determining a point includes a step of calculating a point based on the average of the positions obtained sequentially; and
the step of determining a direction of the object on an image includes a step of calculating the direction based on the direction of the object in time series acquired sequentially.

8. The method of image processing, according to claim 5, wherein:
the step of matching the average of the positions includes a step of generating a background difference image sequentially based on a time difference between the time-series radiation images; and
the step of matching the average of the positions includes a step of using an adjusted image obtained by aligning the background difference image as the correction image.

9. The method of image processing, according to claim 5, wherein:
the step of matching the average of the positions includes a step of generating time-integrated correction images sequentially by performing time integration on the time-series correction image.

10. A method of image processing, comprising the steps of:
- acquiring a position of a feature point in a given object for each of a plurality of sequentially taken radiographic images;
- identifying trajectories formed by the sequentially acquired feature points;
- determining a point on each radiographic image within a range of the identified trajectory;
- matching positions of the feature points on the radiation images to the determined point, thereby generating correction images;
- wherein the step of matching the positions of the feature points includes a step of generating a background difference image sequentially based on a time difference between the time-series radiation images; and
- wherein the step of matching the positions of the feature points includes a step of using an adjusted image obtained by aligning the background difference image as the correction image.

11. The method of image processing, according to claim 10, wherein:
- the step of matching the positions of the feature points includes a step of generating time-integrated correction images sequentially by performing time integration on the time-series correction image.

\* \* \* \* \*